United States Patent
Wo et al.

(10) Patent No.: US 11,202,594 B2
(45) Date of Patent: Dec. 21, 2021

(54) STIMULUS INFORMATION COMPILING METHOD AND SYSTEM FOR TESTS

(71) Applicant: BEIJING HUANDU INSTITUTE OF WISDOM-MIND TECHNOLOGY LTD., Beijing (CN)

(72) Inventors: Jianzhong Wo, Beijing (CN); Yang Liu, Beijing (CN)

(73) Assignee: BEIJING HUANDU INSTITUTE OF WISDOM-MIND TECHNOLOGY LTD., Beijing (CN)

(*) Notice: Subject to any disclaimer, the term of this patent is extended or adjusted under 35 U.S.C. 154(b) by 0 days.

(21) Appl. No.: 17/021,182

(22) Filed: Sep. 15, 2020

(65) Prior Publication Data

US 2020/0405210 A1    Dec. 31, 2020

Related U.S. Application Data

(63) Continuation of application No. 15/748,308, filed as application No. PCT/CN2016/082805 on May 20, 2016, now abandoned.

(30) Foreign Application Priority Data

Aug. 7, 2015  (CN) .......................... 201510483487.8
Aug. 7, 2015  (CN) .......................... 201510484817.5
(Continued)

(51) Int. Cl.
*A61B 5/16* (2006.01)
*A61B 5/00* (2006.01)
(Continued)

(52) U.S. Cl.
CPC ................ *A61B 5/162* (2013.01); *A61B 3/02* (2013.01); *A61B 5/0053* (2013.01);
(Continued)

(58) Field of Classification Search
None
See application file for complete search history.

(56) References Cited

U.S. PATENT DOCUMENTS

2005/0089206 A1    4/2005   Rice et al.
2007/0134631 A1*   6/2007   Hardy ...................... G09B 7/02
                                                    434/236
(Continued)

FOREIGN PATENT DOCUMENTS

CN       102293656        12/2011
CN       103561651         2/2014
(Continued)

OTHER PUBLICATIONS

International Search Report and Written Opinion of the International Searching Authority of Application No. PCT/CN2016/082805 dated Aug. 24, 2016.
(Continued)

*Primary Examiner* — Jerry-Daryl Fletcher
*Assistant Examiner* — Daniel E Lane
(74) *Attorney, Agent, or Firm* — Michael Ye; Rimon Law

(57) ABSTRACT

The present invention relates to a stimulus information compiling method for tests, characterized in that, the stimulus information compiling method comprises the following steps: selecting and using stimulus information which follows a statistics-normal distribution and is analyzed and measured by validity to form a stimulus information database (Q); reasonably setting at least one stimulus information to be a test including at least one test sequence, for a subject to make a selection according to his or her personal interests; comparing a test score of the subject with that of a valid sample person in a normal distribution model, thereby confirming the distribution of the subject in each cognitive dimension. The present invention compares a test score of the subject with that of a valid sample person in a
(Continued)

normal distribution model, thereby confirming the test result of the subject.

3 Claims, 8 Drawing Sheets

(30) Foreign Application Priority Data

| Aug. 7, 2015 | (CN) | 201510484818.X |
|---|---|---|
| Aug. 7, 2015 | (CN) | 201510484820.7 |
| Aug. 7, 2015 | (CN) | 201510484832.X |
| Aug. 7, 2015 | (CN) | 201510484841.9 |

(51) Int. Cl.

| *A61B 5/0205* | (2006.01) |
|---|---|
| *A61B 5/11* | (2006.01) |
| *G06F 16/435* | (2019.01) |
| *G16B 50/00* | (2019.01) |
| *A61B 5/18* | (2006.01) |
| *G16H 10/20* | (2018.01) |
| *A61B 3/02* | (2006.01) |
| *A61B 5/12* | (2006.01) |
| *H04L 29/06* | (2006.01) |

(52) U.S. Cl.
CPC .......... *A61B 5/0075* (2013.01); *A61B 5/0205* (2013.01); *A61B 5/11* (2013.01); *A61B 5/1123* (2013.01); *A61B 5/12* (2013.01); *A61B 5/163* (2017.08); *A61B 5/164* (2013.01); *A61B 5/165* (2013.01); *A61B 5/167* (2013.01); *A61B 5/18* (2013.01); *A61B 5/4011* (2013.01); *G06F 16/435* (2019.01); *G16B 50/00* (2019.02); *G16H 10/20* (2018.01); *H04L 63/0428* (2013.01)

(56) References Cited

U.S. PATENT DOCUMENTS

| 2007/0134632 | A1* | 6/2007 | Chan | G09B 7/02 434/236 |
|---|---|---|---|---|
| 2007/0134633 | A1* | 6/2007 | Chan | G09B 7/02 434/236 |
| 2007/0134634 | A1* | 6/2007 | Chan | G09B 19/00 434/236 |
| 2007/0134636 | A1* | 6/2007 | Chan | G09B 7/00 434/262 |
| 2007/0141541 | A1* | 6/2007 | Chan | G09B 5/06 434/236 |
| 2009/0024050 | A1* | 1/2009 | Jung | G16H 40/67 600/544 |

FOREIGN PATENT DOCUMENTS

| CN | 103873854 | 6/2014 |
|---|---|---|
| CN | 104992080 | 10/2015 |
| CN | 105011952 | 11/2015 |
| CN | 105025036 | 11/2015 |
| CN | 105105772 | 12/2015 |
| CN | 105139317 | 12/2015 |

OTHER PUBLICATIONS

U.S. Appl. No. 15/748,308, filed Jan. 29, 2018, Pending.

* cited by examiner

| second flag value 1 | encryption algorithm 1 |
|---|---|
| second flag value 2 | encryption algorithm 2 |
| ⋮ | ⋮ |
| second flag value n | encryption algorithm n |

| first flag value 1 | encryption key 1 | decryption key 1 |
|---|---|---|
| first flag value 2 | encryption key 2 | decryption key 2 |
| ⋮ | ⋮ | ⋮ |
| first flag value n | encryption key n | decryption key n |

STIMULUS INFORMATION COMPILING METHOD AND SYSTEM FOR TESTS

This application is a continuation application of U.S. patent application Ser. No. 15/748,308, filed Jan. 29, 2018, which is a National Stage Application of PCT/CN2016/082805, filed May 20, 2016, which claims priority to Chinese Patent Application No. 201510483487.8, filed on Aug. 7, 2015, Chinese Patent Application No. 201510484841.9, filed on Aug. 7, 2015, Chinese Patent Application No. 201510484832.X, filed on Aug. 7, 2015, Chinese Patent Application No. 201510484820.7, filed on Aug. 7, 2015, Chinese Patent Application No. 201510484818.X, filed on Aug. 7, 2015, and Chinese Patent Application No. 201510484817.5, filed on Aug. 7, 2015. The entirety of the aforementioned applications is incorporated herein by reference.

FIELD OF THE INVENTION

The present invention relates to the fields of cognitive tests, particularly to stimulus information compiling method and system for tests.

BACKGROUND OF THE INVENTION

Patent (CN 104363948 A) discloses a stimulus presentation system, which discriminates psychological states by calculating and measuring lines of sight and brain functions of a user, and changes a presentation content of an object based on the discriminated psychological states. It solves a technical problem that where it is inferred that the user pays attention to or focuses on something, it cannot be inferred whether due to a concern or due to a perceived danger. Although this system can present various stimulus information, it does not disclose the method of compiling stimulus information or the stimulus information is not completely suitable for a cognitive ability value test.

China patent (publication number: CN 103211605 B) discloses a psychological test system and method. This system includes a human eye image capturing device which compresses and encodes the captured human eye images and then transmits to a host subsystem; and the host subsystem which processes every received human eye image, and matches with a sample stored in the system, the psychological states represented by the sample with the highest matching degree with a test sample being the psychological states of the test sample. This test method mainly applies pupil area analyzing and positioning, information modeling, a principal component analyzing method, and a mode recognition and sorting method to determine the psychological states of a subject. This test system and test method have the following defects: (1) the stimulus information in this patent is similar to that of a general questionnaire, and the selection of the stimulus information lacks scientificity such that it is difficult to objectively evaluate the psychological quality of the subject when facing infinite stimulus information; (2) the stimulus information provided by this patent can only be presented to the subject visually such that this system and method are not suitable for special population such as the visually impaired and the hearing and speech impaired.

Patent CN101902963B discloses a personality examination device which employs a system being an MMPI that examines the personality, that is, the Minnesota Multiphasic Personality Inventory. However, what is represented by most inventories of the MMPI is a pathopsychological concept which is mainly used for distinguishing a psycho-path from a normal person. Therefore, its range of application is limited, thereby limiting to a certain extent the research on personalities of healthy people.

Chinese patent CN201310058619.3 provides a cognitive curve generating system based on a video. The system learns which part in the video more easily catches the attention of persons by testing a change in pupils of a person who is watching the video, and is mainly used for advertisement and propaganda films, in order to analyze how to draw peoples' attention more easily, thereby increasing an interest rate. However, this system can only test the place where a person is attracted in a specific environment, which is a relative interest set off by the environment. Its range of application is narrow, and the system cannot test the long-term stable interest of a person in daily life. Moreover, different persons have different understanding on the same thing, so the subject may have different understanding on his or her concerned things in the video from what is understood by a data analyzer, thereby causing misunderstanding and lowering the accuracy of the test result.

Patent document (CN 103440864 A) discloses a personality feature prediction method based on voice, which establishes a voice personality prediction machine learning model in advance, uses any voice clip provided by the user to realize the personality feature prediction by using the voice personality prediction machine learning model, establishes a mapping relationship between a voice feature and the personality feature factor by a statistical learning method, and predicts each item of personality index. Although this patent overcomes the shortcomings in terms of written answer sheet such as time consuming, effects being influenced by subjective factors, and inconvenient acquisition of determination materials, the technical means of only using the voice material to predict the personalities is still monotonous. The voice feature is susceptible to the physiology and surroundings of the user, has deviation in reflecting the personality characteristics, and is uncertain to reflect the real personality characteristic. Therefore, this patent has monotonous test materials and cannot exclude the test error caused by the influence of the surroundings.

SUMMARY OF THE INVENTION

According to one aspect of the present invention, the present invention provides a stimulus information compiling method for tests, characterized in that, the stimulus information compiling method includes the following steps:

selecting and using stimulus information which follows a statistics-normal distribution and is analyzed and measured by validity to form a stimulus information database;

reasonably setting at least one stimulus information to be a test including at least one test sequence, for a subject to make a selection according to his or her personal interests;

comparing a test score of the subject with that of a valid sample person in a normal distribution model, thereby confirming the distribution of the subject in each cognitive dimension.

According to one preferred embodiment, the forming a stimulus information database includes the following steps:

creating a first preselected stimulus information database;

making the first screening for the sampled persons, and selecting the stimulus information with the test result following the normal distribution to create a second preselected stimulus information database;

making the second screening on the stimulus information in the second preselected stimulus information database for the subjects with different ages, different races, difference blood types and/or different cultural backgrounds, and selecting the stimulus information with the test result following the normal distribution to create a third preselected stimulus information database;

sorting the stimulus information in the third preselected stimulus information database, and randomly inserting at least one lie detection stimulus information in each type of the stimulus information to create the stimulus information database so as to obtain the stimulus information of the test.

According to one preferred embodiment, the stimulus information compiling method further includes:

dynamically adjusting a test sequence of the stimulus information based on the physiological information and/or psychological state of the subject, thereby obtaining a real test result of the subject maintaining good psychological states;

dynamically inserting guiding stimulus information based on the physiological information and/or psychological state of the subject, thereby guiding the subject's bad psychological states to restore to be good.

According to one preferred embodiment, the stimulus information compiling method further includes:

adjusting and controlling a presentation speed of the stimulus information based on the recorded response time index of the subject in the test process, and measuring the serious degree of the subject by the response time index and guiding the subject to adjust the serious degree, wherein the way of guiding the subject to adjust the serious degree includes alarming and/or presenting the guiding stimulus information.

According to one preferred embodiment, the stimulus information includes virtual reality scene information making the subject blend in the real scene, the virtual reality scene information at least including auditory stimulus information, visual stimulus information, olfactory stimulus information and/or tactile stimulus information, wherein the tactile stimulus information includes braille tactile stimulus information.

According to one preferred embodiment, the stimulus information compiling method includes presenting visual and/or auditory and/or tactile stimulus information to the subject by a stimulus information providing device, respectively recording the response time index and/or body movement change and/or acoustic wave information of the subject in the process of processing the stimulus information by including a response tracking device and a response time control device and/or a sound transmission feedback device, the recorded information collectively processed by an analytical processing device and its result fed back to a display device.

According to one preferred embodiment, the response tracking device compares the body movement change presented by the subject in the process of processing the stimulus information with each recorded action feature and/or normal action feature by adopting application data and/or an analyzing system through an infrared camera, to record the conversion of the action feature.

According to one preferred embodiment, the stimulus information compiling method further includes:

obtaining first analytical data by analyzing the feedback information and/or response time index and/or body movement change and/or acoustic wave information of the subject recorded by the stimulus information providing device;

correcting in an auxiliary way, by the first analytical data, second analytical data obtained for inherent feedback information directly entered by the subject through an information entering device;

determining the analytical result generated by the subject for each group of stimulus according to the first analytical data and the second analytical data, such that a storing device makes an operation of whether to flag this group of stimulus according to an attribute of the analytical result.

According to one preferred embodiment, the analytical result includes a positive analytical result and a negative analytical result, if the attribute of the analytical result is positive, the analytical result is a positive analytical result, and the storing device stores the positive analytical result and this group of stimulus corresponding thereto;

if the attribute of the analytical result is negative, the analytical result is a negative analytical result, and the storing device stores and flags the negative analytical result and this group of stimulus corresponding thereto.

According to one preferred embodiment, the storing device feeds back at least one group of flagged stimulus to the stimulus information providing device, the stimulus information providing device matches the similar or related alternative stimulus information from the stimulus information database to be provided to the subject for continued tests according to the at least one group of flagged stimulus, and the test is not completed until the number of flagged stimulus reduces to within the predetermined range.

According to one preferred embodiment, the infrared camera captures random feedback information generated by the subject according to each group of stimulus, the random feedback information including facial micro-expression, the infrared camera fast transfers the micro-expression image of the subject bearing the current stimulus information to the analytical processing device.

According to one preferred embodiment, screening one or more micro-expressions with low probability of occurrence according to a statistical method from a micro-expression image group consisting of several micro-expressions by a preprocessing unit of the analytical processing device, to match with several sample micro-expressions in the micro-expression database of the analytical processing device, thereby determining the first analytical data according to several sample micro-expressions pre-stored in the micro-expression database and the psychological features corresponding thereto.

According to one preferred embodiment, the inherent feedback information is answer information provided by the subject according to several test questions providing the stimulus information and entered by the information entering device, the analytical processing device calculating the cognitive index value and generating the second analysis data according to the answer information and the stimulus corresponding thereto.

According to one aspect of the present invention, the present invention provides a stimulus information compiling method for cognitive ability value tests, characterized in that, the stimulus information compiling method at least includes:

selecting at least one stimulus information of the sample persons whose test validity follows the normal distribution;

setting at least one reasonable sorting based on the validity and cognitive dimension of the at least one stimulus information, for the subject to make a selection according to personal interests;

dynamically compiling lie detection stimulus information and/or aversive stimulus information according to the physiological information and/or psychological states of the subject;

comparing a test score of the subject with that of a valid sample person in a normal distribution model, thereby confirming the distribution of the subject in each cognitive dimension.

According to one preferred embodiment, the stimulus information compiling method further includes:

dynamically adjusting a test sequence of the stimulus information based on the physiological information and/or psychological states of the subject, thereby obtaining a real test result of the subject maintaining good psychological states.

According to one preferred embodiment, the step of selecting at least one stimulus information of the sample group whose test validity follows the normal distribution at least includes:

setting at least one stimulus information based on a psychological feature parameter in each cognitive dimension;

testing the sample persons by the at least one stimulus information and obtaining the sample validity;

testing the sample validity using the normal distribution model;

retaining the at least one stimulus information with the sample validity following the normal distribution model.

According to one preferred embodiment, the selecting at least one stimulus information of the sample group whose test validity follows the normal distribution at least includes:

making the second test on the at least one stimulus information with the sample validity following the normal distribution model for the sample persons with different races, different ages, different blood types and/or different cultural backgrounds;

selecting the at least one stimulus information with the second sample validity following the normal distribution model.

According to one preferred embodiment, the stimulus information compiling method further includes:

dynamically inserting guiding stimulus information based on the physiological information and/or psychological state of the subject, thereby guiding the subject's bad psychological states to restore to be good.

According to one preferred embodiment, the stimulus information compiling method further includes:

adjusting and controlling a presentation speed of the stimulus information based on the recorded response time index of the subject in the test process, and measuring the serious degree of the subject by the response time index and guiding the subject to adjust the serious degree, wherein the way of guiding the subject to adjust the serious degree includes alarming and/or presenting the guiding stimulus information.

According to one preferred embodiment, the physiological information at least includes brain information, facial muscle movement information, eye ball movement information, body action information, acoustic wave information, response time information, pulse information, blood pressure information and/or body temperature information.

According to one preferred embodiment, the stimulus information includes virtual reality scene information making the subject blend in the real scene, the virtual reality scene information at least including auditory stimulus information, visual stimulus information, olfactory stimulus information and/or tactile stimulus information.

According to one preferred embodiment, the stimulus information is holographic scene stimulus information at least including the auditory stimulus information and the holographic image stimulus information matched therewith, the holographic scene stimulus information presenting the real scene stimulus in a way of three-dimensional stereoscopic image, thereby obtaining the real-time cognitive ability test value of the subject;

wherein the holographic image stimulus information includes a static holographic image and a dynamic holographic image.

According to one preferred embodiment, the tactile stimulus information includes braille tactile stimulus information.

According to another aspect of the present invention, the present invention provides a stimulus information compiling method for a potential value test, the stimulus information compiling method including the following steps:

creating a first preselected stimulus information database;

making the first screening for the sampled persons, selecting the stimulus information with the test result following the normal distribution to create a second preselected stimulus information database;

making the second screening on the stimulus information in the second preselected stimulus information database for the subjects with different ages, different races, difference blood types and/or different cultural backgrounds, and selecting the stimulus information with the test result following the normal distribution to create a third preselected stimulus information database;

sorting the stimulus information in the third preselected stimulus information database, and randomly inserting at least one lie detection stimulus information in each type of the stimulus information to create the stimulus information database so as to obtain the stimulus information of the potential value test.

According to one preferred embodiment, the first preselected stimulus information database is created in the following way: at least setting fourteen dimensions of the ability of handling and operating, the ability to organize and manage, language competence, interpersonal skill, natural cognition ability, artistic ability, working memory capacity, information processing ability, image ability, music ability, logic reasoning ability, spatial ability, mathematics ability and thinking transformation ability by analyzing potency, and respectively setting a group of stimulus information for the fourteen dimensions to form the first preselected stimulus information database.

According to one preferred embodiment, the stimulus information content in the fourteen dimensions includes stems of the stimulus information and the options fed back by the subject, and the content of the stimulus information further includes the objective description on the stimulus information, such that the subject can give the correct feedback in the case of making clear the meaning of the stimulus information.

According to one preferred embodiment, the options provided to the subject for feedback by the stimulus information of the ability of handling and operating, the stimulus information of the language competence, the stimulus information of the natural cognition ability, the stimulus information of the artistic ability, the stimulus information of working memory capacity, the stimulus information of information processing ability, the stimulus information of image ability, the stimulus information of music ability, the stimulus information of logic reasoning ability, the stimulus information of spatial ability, the stimulus information of mathematics ability and the stimulus information of thinking transformation ability are set in a way of interval scale and ratio scale, the options provided to the subject for feedback by the stimulus information of the ability to organize and manage and the stimulus information of interpersonal skill are set in a way of interval scale.

According to one preferred embodiment, the stimulus information is sorted and stored in the stimulus information storing unit of the storing device according to the type of the stimulus information and/or format of the stimulus information, the stimulus information is extracted by the stimulus information providing device and is presented to the subject in a way of visual stimulus information, auditory stimulus information and/or tactile stimulus information.

According to one preferred embodiment, the play speed and/or number of times to play of the stimulus information is autonomously controlled by the subject through a potential value testing system, and the visual stimulus information is provided to the subject by the visual stimulus information providing unit of the stimulus information providing device, the visual stimulus information providing unit is a computer display, a tablet computer or a mobile phone display screen; the auditory stimulus information is provided to the subject by the auditory stimulus information providing unit of the stimulus information providing device, the auditory stimulus information providing unit is an earphone, a sound system or a loudspeaker device; the tactile stimulus information is provided to the subject by the tactile stimulus information providing unit of the stimulus information providing device, the tactile stimulus information providing unit is an image tactile device, a sound tactile device or a braille operation device.

According to one preferred embodiment, the stimulus information compiling method further includes the following steps: storing the physiological feature in the feedback to the stimulus information to the physiological feature model unit of the storing device, such that when the potential value test is performed, the infrared autotracking camera of the control device records the physiological feature presented when the subject feeds back the stimulus information, and comparing the physiological feature with the physiological feature index fed back to the corresponding stimulus information stored in the physiological feature model unit, to determine the reliability level of the feedback given by the subject to the stimulus information.

According to one preferred embodiment, the stimulus information compiling method further includes the following steps: storing the response time index feeding back to the stimulus information in the response time index storing unit of the storing device, so that when the potential value test is performed, the time when the subject feeds back to the stimulus information is recorded by the control device, and comparing the feedback time with the response time index feeding back to the corresponding stimulus information stored in the response time index storing unit, and giving alarm to the stimulus information not fed back within the response time index by the control device, in order to ensure the reliability level of the feedback given by the subject to the stimulus information.

According to one preferred embodiment, after the stimulus information is presented to the subject by the stimulus information providing device, the feedback data collecting device collects the feedback of the subject to the stimulus information and sends to the storing device, at the same time, the control device records the physiological feature presented when the subject feeds back the stimulus information, and sends to the storing device, the storing device performs data processing on the feedback to the stimulus information and the physiological feature of the subject, to get the potential evaluation index value, and the potential evaluation index value is supplied to the display device by the data transmission device, and the data transmission device automatically transmits the stimulus information to the stimulus information providing device, so that the stimulus information is presented to the next subject to be tested.

According to one preferred embodiment, the method of the storing device performing data processing on the feedback to the stimulus information collected by the feedback data collecting device and the physiological feature of the subject recorded by the control device is as follows: matching the feedback to the stimulus information within the range of reliability level with the stimulus information feedback index stored in the stimulus information feedback unit of the storing device according to the reliability level on the feedback to the stimulus information determined by the physiological feature to get the evaluation index value of each stimulus information, and summarizing the evaluation index values in each dimension by the data analyzing unit of the storing device in order to get the potential evaluation index value.

According to another aspect of the present invention, the present invention provides a stimulus information compiling method for personality characteristic value tests following the personality of the eastern. The personality characteristic value evaluation parameter of the subject is acquired by selecting and using the question test and/or scene test following the statistic normal distribution and measured by validity analysis, and the characteristic values of the subject are acquired in at least 27 dimensions from at least five different extents for an ordering index and/or a ratio index of the evaluation parameter.

According to one preferred embodiment, the question test and/or scene test of each dimension of the at least 27 dimensions at least includes one reverse question;

the validity analysis measure at least includes a discrimination validity measure, an empirical validity measure and a criterion validity measure;

the at least 27 dimensions at least includes accountability and carelessness, loyalty and mutability, industriousness and laziness, optimism and apprehension, ascendance and submissiveness, gregariousness and solitude, straightforwardness and sophistications, autorhythmicity and randomness, social boldness and shrink, prudence and impertinency, ordering and disordering, independence and dependence, enthusiasm and indifference, credibility and suspiciousness, flexibility and rigidity, curiosity and indifference, persistence and looseness, altruism and egoism, agreeableness and hostility, patience and impatience, fairness and eccentricity, aestheticism and popularity, mobility and leisure, imagination and reality, sympathy and intellectuality, stabilization and tension, as well as sensibility and bluntness.

According to one preferred embodiment, the method further includes acquiring the personality characteristic value evaluation parameter of the subject in a way of tactile presenting stimulus, the way of tactile presenting stimulus including braille presentation, the stimulus information presented by the braille is the question test and/or scene test following the statistic normal distribution and measured by validity.

According to one preferred embodiment, the method further includes acquiring the evaluation parameter of the personality characteristic value of the subject in the way of auditory presenting stimulus, the way of auditory presenting stimulus including voice presentation, the stimulus information presented by the voice presentation is the question test and/or scene test following the statistic normal distribution and measured by validity.

According to one preferred embodiment, each question test and/or scene test following the statistic normal distribution and measured by validity respectively corresponds to the specific response time index, the response time index being used for detecting the serious operation behavior of the subject.

According to one preferred embodiment, the method includes presenting visual and/or auditory and/or tactile stimulus information to the subject by a stimulus information providing device, respectively recording the response time and/or body movement change and/or acoustic wave information of the subject in the process of processing the stimulus information by including a response tracking device and a response time control device and/or a sound transmission feedback device, the recorded information collectively processed by an analytical device and its result fed back to a display device.

According to one preferred embodiment, the response tracking device compares the body movement change presented by the subject in the process of processing the stimulus information with each recorded action feature and/or normal action feature by adopting application data and/or an analyzing system through an infrared camera, to record the conversion of the action feature.

According to one preferred embodiment, the response time control device can further record the response time index of each test question, and detects in time the serious operation action of the subject in a way of alarm.

According to one preferred embodiment, the body movement includes eye ball movement, facial muscle movement and/or movement of other parts of the body.

According to one preferred embodiment, the method includes the following steps:

generating the test stimulus information in order according to the operation control of the operation control device by the stimulus information providing device, the subject selecting the degree options of the real situation of the subject according to the test stimulus information;

recording, by the response time control device, the response time and the response time index of the subject during the test; recording, by the response tracking device, the actions of the body of the subject during the test; recording, by the sound transmission feedback device, the sound test data of the subject;

performing, by the analyzing device, data merge, processing conversion to get the characteristic value of the subject.

According to another aspect of the present invention, the present invention provides an interest orientation value testing method, particularly provides a stimulus information compiling method for the interest orientation value tests, the method including the following steps:

(1) providing quizzes to the subject, the quizzes containing the stimulus information related to the potential interest of the subject, and a plurality of descriptions of the stimulus information;

(2) selecting, by the subject, one or more descriptions for each quiz according to his or her own understanding, as the feedback information of the subject;

(3) acquiring the physiological response information and time information of the subject to the stimulus information;

(4) processing the stimulus information, the feedback information of the subject, the physiological response information and time information, to get the interest orientation of the subject;

wherein the description includes an objective description and/or a tendentious description of the stimulus information content; the time information is the experience time of the subject to a certain stimulus information, and/or the duration time of a certain physiological response.

According to one preferred embodiment, the subject autonomously controls the play speed and/or number of times to play of the stimulus information, the experience time including the play speed and/or number of times to play, and the experience time can reflect the time the subject pays attention to the stimulus information.

According to one preferred embodiment, the stimulus information is sorted according to the information format and/or the content contained therein.

According to one preferred embodiment, the stimulus information is matched with the physiological response time and the time information, to get the experience time, the physiological response and duration time of the subject to each type of stimulus information.

According to one preferred embodiment, the stimulus information is grouped according to the feedback information of the subject.

According to one preferred embodiment, the stimulus information is matched with the physiological response time and the time information, to get the experience time, the physiological response and duration time of the subject to each group of stimulus information.

According to one preferred embodiment, different weights are respectively given to the experience time, the physiological response and duration time of each type of stimulus information and/or each group of stimulus information.

According to one preferred embodiment, the interest tendency of the subject is obtained according to the experience time, the physiological response and duration time of the subject to each type of stimulus information and/or each group of stimulus information and the weights.

According to one preferred embodiment, the stimulus information is one or more of a picture, a video and an audio.

According to one preferred embodiment, the physiological response information is one or more of pupil diameter, galvanic skin response, pulse, blood pressure, and brain wave information of the subject.

According to another aspect of the present invention, the present invention provides a cognitive ability test value encrypting and transmitting method based on internet, the method at least including: when the remote server encrypts the generated test report, randomly generating, by a first key managing module pre-storing at least one key pair, a first flag value representing the encryption key when a remote server encrypts the generated test report; converting, by a first encryption module pre-storing at least one encryption algorithm, the test report to a first cryptograph according to its randomly selected encryption algorithm and the first flag value, the encryption module having therein a second flag value corresponding to the encryption algorithm one by one; sending, by the first transmission module, the first cryptograph, the first flag value and the second flag value to a client; converting, by the client, the first cryptograph to the plaintext test report according to first flag value and the second flag value.

According to one preferred embodiment, the method includes: acquiring, by a second decryption module located at the client, a decryption key corresponding to the encryption key according to the first flag value, and acquiring a decryption algorithm corresponding to the encryption algorithm according to the second flag value, thereby decrypting the first cryptograph according to the decryption algorithm and the decryption key.

According to one preferred embodiment, the method further includes: separately sending, by the first transmission module, the first cryptograph and the first flag value and/or second flag value to the client.

According to one preferred embodiment, the method further includes: connecting in series, by the first transmission module, the first flag value and/or second flag value at the front end or tail end of the first cryptograph and sending to the client.

According to one preferred embodiment, the method further includes: assigning, by the first transmission module, one same random number to the first cryptograph, the first flag value and the second flag value where the first cryptograph, the first flag value and the second flag value are sent separately.

According to one preferred embodiment, the method further includes: converting, by a second encryption module provided at the client, the test answer of a testee into the second cryptograph and sending to the remote server, the first decryption module of the remote server decrypting the second cryptograph to get the plaintext test answer.

According to one preferred embodiment, the method further includes: separately encrypting, by the second encryption module, the test answer of each testing module in the process of testing the testee and then combining in series the encrypted cryptograph to form the second cryptograph.

According to one preferred embodiment, the method of separately encrypting the test answer of each testing module specifically includes: converting, by the second encryption module, the test answer of the testing module to the cryptograph according to its randomly selected encryption algorithm and the encryption key randomly generated by the second key managing module after the testee completes one testing module, and the cryptograph including the second flag value corresponding to the selected encryption algorithm and the first flag value corresponding to the selected encryption key.

According to the one preferred embodiment, the method further includes: after separately encrypting each testing module to form a cryptograph, connecting in series the cryptograph corresponding to each testing module to make the secondary encryption to form the second cryptograph.

According to one perfected embodiment, the method further includes: inquiring the testee whether to send the test report before the test report is sent to the client, and sending the test report after the testee enters the pre-set personal password.

According to another aspect of the present invention, the present invention provides a driver top speed assessing system, including:

a stimulus information generating module, for generating stimulus information consisting of a sound, image, video and/or vibration displacement to the subject;

a feedback information collecting module, for collecting feedback information initially given by the subject and/or given in response to the stimulus information;

a speed analyzing module, including a response speed unit, an attention extent unit and a hand-foot-eye coordinating unit, the speed analyzing module making an analysis and obtaining the top speed of the subject based on the stimulus information and the feedback information and in combination with the stored standard database.

According to one preferred embodiment, the response speed unit, the attention extent unit and the hand-foot-eye coordinating unit respectively calculate first, second and third data according to the stimulus information and the feedback information and in combination with the standard database, the speed analyzing module obtaining the top speed after performing weighting on the first to third data.

According to one preferred embodiment, the assessing system includes a center control device connected with the stimulus information generating module and the feedback information collecting module, The display device and the speaker device in the stimulus information generating module output the stimulus information consisting of sound, image and/or video according to the control signal output by the center control device; the feedback information collecting module includes a steering wheel with buttons, a pedal plate, a mobile phone receiver, a network transmission device, a camera and an eye tracker, the feedback information collecting module regularly or irregularly collects the feedback information according to the time index of the stimulus information generating module outputting stimulus information and/or a sampling instruction sent by the center control device, and transmits them to the speed analyzing module.

According to one preferred embodiment, the stimulus information generating module generates the sound, image and/or video information for measuring the response speed, the feedback information collecting module samples the first feedback information which is fed back by the subject in response to the stimulus information and includes the operation action, eye movement index, and respectively records its time data, the response speed unit processes the first feedback information with the time data, to get the response speed and the emergency response speed of the subject, and gets the first data after weighting.

According to one preferred embodiment, the stimulus information generating module respectively generates the first and second visual stimulus information at the central field of view and the peripheral field of view of the subject, and performs the cross transform in a way of descending time period, the feedback information collecting module samples the operation action, head movement index and eye movement index of the subject, and take them as the second feedback information to be stored, the attention extent unit makes an analysis according to the second feedback information, the first and the second visual stimulus information and in combination with the attention threshold data in the standard database to obtain the second data.

According to one preferred embodiment, the display device of the stimulus information generating module generates a simulative driving scene periodically changing with time, so that the subject performs the simulative driving operation, the feedback information collecting module collects the hand action, foot action, and eye movement index of the subject, and stores them as the third feedback information, the hand-foot-eye coordinating unit makes an analysis according to the third feedback information and/or the driving simulated data and in combination with the coordination data in the standard database to obtain the third data.

According to one preferred embodiment, the speed analyzing module further includes an emotion analyzing unit, the stimulus information generating module gives the stimulus information which periodically changes with time and contains the video and vibration displacement to the subject, the feedback information collecting module collects the fourth feedback information at least including the microexpression data and the brain wave data, the emotion analyzing unit makes an analysis according to the stimulus information strength, the fourth feedback information and the emotion data in the standard database to obtain the emotion control data of the subject, the speed analyzing module performs the weighting on the first to third data and the emotion control data to obtain the top speed.

According to one preferred embodiment, the speed analyzing module further includes a driving action determining unit, the driving action determining unit making an analysis according to the feedback information and the stimulus information to obtain the driving behavior data of the subject, the driving behavior data at least includes the following distance and the relative speed, the speed analyzing module correcting the top speed according to the driving behavior data.

According to one preferred embodiment, the speed analyzing module makes an analysis according to the age of the subject and the measured top speed and in combination with the experience distribution model in the standard database to get the predicted top speed of the subject within one measurement period.

A driver top speed assessing method, including the following steps:

generating, by a stimulus information generating module, stimulus information consisting of a sound, image, video and/or vibration displacement to the subject;

collecting, by a feedback information collecting module, feedback information initially given by the subject and/or given in response to the stimulus information;

making an analysis, by a speed analyzing module, based on the stimulus information and the feedback information and in combination with the stored standard database to obtain the top speed of the subject, wherein the response speed unit, the attention extent unit and the hand-foot-eye coordinating unit respectively calculate first, second and third data according to the stimulus information and the feedback information and in combination with the standard database, the speed analyzing module obtaining the top speed after performing weighting on the first to third data.

REFERENCE NUMERALS

Figure 1:
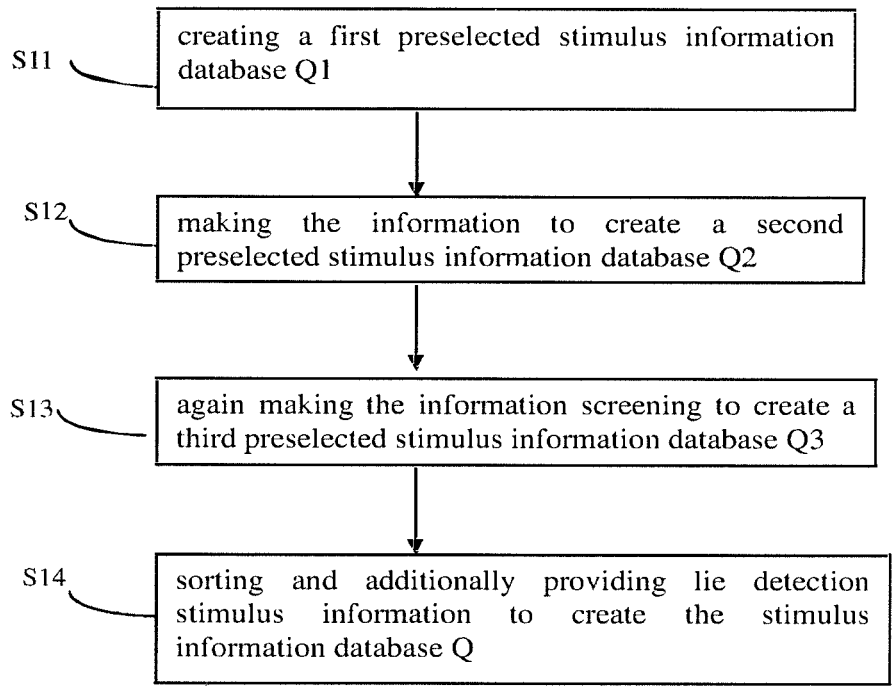
FIG. 1 shows the steps of the stimulus information compiling method for potential value tests of the present invention.

Q1: first preselected stimulus information database
Q2: second preselected stimulus information database
Q3: third preselected stimulus information database
Q: stimulus information database
100: stimulus information providing device
200: feedback data collecting device
300: control device
400: storing device
500: data transmitting device
101: visual stimulus information providing unit
102: auditory stimulus information providing unit
103: tactile stimulus information providing unit
201: reactor unit
401: stimulus information storing unit
402: response time index storing unit
403: stimulus information feedback unit
404: physiological feature model unit
405: data analyzing unit
10: stimulus information presenting device
11: visual presentation stimulus device
12: sound presentation stimulus device
13: tactile presentation stimulus device
14: response time control device
15: operation control device
16: sound transmission feedback device
17: response tracking device
18: analytical processing device
19: test project unit
20: response time unit
21: eye movement trace unit
22: body action unit
23: acoustic wave message unit
24: answer unit
25: data summarizing unit
26: data transferring unit
27: display device

DETAILED DESCRIPTION OF THE EMBODIMENTS

The detailed description is made below in combination with the drawings.

The stimulus information (also referred to as stimulus) of the present invention refers to the information such as a character, figure, animation and sound. The stimulus information contains contents involving various aspects of human brain cognition such as memory, mathematics, language, space, image, painting, music, logic reasoning, and is provided to the subject in a form of image, character or sound, and tends to contain a feedback prompt. Each group of stimulus includes a plurality of quizzes related to abilities.

The "interval index" in the present invention refers to the measurement made to an absolute difference of the statistic object, that is to set different scores to the options representing the cognitive abilities in different degrees. For example, the option representing the best cognitive ability is set to be a score of 5, and the option representing the worst cognitive ability is set to be a score of 1.

The "ordering index" in the present invention refers to a numeric type variable of the measurement made to an order difference of the statistic object, a numeral value or a symbol indicating the degree of something, for example, indicating a response dimension in the cognitive ability, and there may have three values of low, medium and high, respectively denoted by 1, 2 and 3. The ordering can also adopt other ways, such as a progress bar form to represent degree.

The "ratio index" in the present invention refers to a numeric type variable of the measurement made to the absolute difference and the order difference of the statistic object. For example, slow, relatively slow, medium, relatively fast, fast are set for the response time, wherein a score of 10 is set for slow, a score of 30 is set for relatively slow, a score of 50 is set for medium, a score of 70 is set for relatively fast, and a score of 90 is set for fast.

The "test dimension" in the present invention refers to an angle for evaluating the cognitive ability. For example, consciousness is a test dimension, reasoning is a test dimension, understanding is a test dimension and attention is a test dimension.

The present invention provides a stimulus information compiling method for cognitive tests, the stimulus information compiling method including the following steps:

S1: selecting and using stimulus information which follows a statistics-normal distribution and is analyzed and measured by validity to form a stimulus information database (Q);

S2: reasonably setting at least one stimulus information to be a test including at least one test sequence, for a subject to make a selection according to his or her personal interests;

S3: comparing a test score of the subject with that of a valid sample person in a normal distribution model, thereby confirming the distribution of the subject in each cognitive dimension.

First Embodiment

According to one preferred embodiment, the forming a stimulus information database (Q) includes the following steps:

S11: creating a first preselected stimulus information database (Q1);

S12: making the first screening for the sampled persons, and selecting the stimulus information with the test result following the normal distribution to create a second preselected stimulus information database (Q2);

S13: making the second screening on the stimulus information in the second preselected stimulus information database (Q2) for the subjects with different ages, different races, difference blood types and/or different cultural backgrounds, and selecting the stimulus information with the test result following the normal distribution to create a third preselected stimulus information database (Q3);

S14: sorting the stimulus information in the third preselected stimulus information database (Q3), and randomly inserting at least one lie detection stimulus information in each type of the stimulus information to create the stimulus information database (Q) so as to obtain the stimulus information of the test.

FIG. 1 shows the steps of the stimulus information compiling method for potential value tests of the present invention. As shown in FIG. 1, the stimulus information compiling method for potential value tests includes the following steps: firstly, selecting the evaluation factor with the greatest influence on the potential test by analyzing the potential. By analyzing and referring to the existing technical research results, fourteen dimensions of the ability of handling and operating, the ability to organize and manage, language competence, interpersonal skill, natural cognition ability, artistic ability, working memory capacity, information processing ability, image ability, music ability, logic reasoning ability, spatial ability, mathematics ability and thinking transformation ability are set as potential evaluation indexes. By analyzing each evaluation index, a group of stimulus information is respectively set for each index, to form the first preselected stimulus information database Q1. Large amounts of stimulus information is contained in the Q1 database, so if information screening is not performed, the subject cannot objectively and clearly give a feedback when facing the large amounts of stimulus information, such that the test result has low reliability. Therefore, the stimulus information in the first preselected stimulus information database Q1 is firstly screened. The stimulus information with the test result following the normal distribution is screened out to create the second preselected stimulus information database Q2. In order to further improve the scientificity of the stimulus information compiling method, the second screening is made on the stimulus information in the second preselected stimulus information database Q2 for the subjects with different ages, different races, difference blood types and/or different cultural backgrounds. The stimulus information with the test result following the normal distribution is screened out to create a third preselected stimulus information database Q3. In order to ensure that the feedback of the subject to the stimulus information has reliability, at least one lie detection stimulus information is randomly inserted in each type of the stimulus information of the third preselected stimulus information database Q3. The stimulus information is sorted and stored in the lie detection stimulus information according to the type of the stimulus information and/or format of the stimulus information to obtain the stimulus information database Q of the potential test. Preferably, the lie detection stimulus information can be aversive stimulus information. The present invention makes screening twice to the stimulus information in the first preselected stimulus information database according to the principle of the normal distribution, the method having scientificity, such that the screened-out stimulus information has reliability and validity, for having high reliability when the potential is tested. Preferably, the present invention respectively sets the corresponding one group of stimulus information for at least fourteen dimensions of the evaluation indexes of the potential according to the characteristics of the subject, such that the stimulus information compiling method provided by the present invention has strong adaptability, and solves the defects that the existing test method introduced from abroad does not follow Chinese cultural characteristics.

Figure 2:
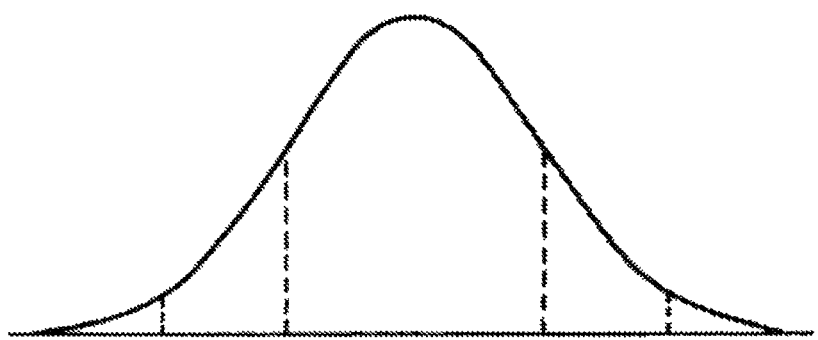
FIG. 2 is a normal distribution diagram met when the stimulus information is screened of the present invention.

FIG. 2 is a normal distribution diagram met when the stimulus information is screened of the present invention. A normal distribution function $$f(x) = \frac{1}{\sqrt{2\pi}\,\sigma} \exp\left(-\frac{(x-\mu)^2}{2\sigma^2}\right)$$

shall be followed when the stimulus information in the first preselected stimulus information database Q1 and the second preselected stimulus information database Q2 is screened. Preferably, a standard normal distribution function $$f(x) = \frac{1}{\sqrt{2\pi}} \exp\left(-\frac{x^2}{2}\right)$$

shall be followed when the stimulus information in the second preselected stimulus information database Q2 is screened. As shown in FIG. 2, the normal distribution curves are in five grades from left to right of very bad, relatively bad, general, relatively good, and very good. For the specific parameter, when the stimulus information in the first preselected stimulus information database Q1 and the second preselected stimulus information database Q2 is screened, only the stimulus information in which it can be selected that 0~5% of the subjects are very bad, 10~20% of the subjects are relatively bad, 50~80% of the subjects are general, 10~20% of the subjects are relatively good and 0~5% of the subjects are very good is satisfactory. It is possible to store this stimulus to the second preselected stimulus information database Q2 or the third preselected stimulus information database Q3. Preferably, when the stimulus information in the second preselected stimulus information database Q2 is screened, only the stimulus information in which it can be selected that 2~2.5% of the subjects are very bad, 13~14% of the subjects are relatively bad, 67~70% of the subjects are general, 13~14% of the subjects are relatively good and 2~2.5% of the subjects are very good is satisfactory. It is possible to store this stimulus to the third preselected stimulus information database Q3. The selection method of the normal distribution has scientificity, the screened-out stimulus information has reliability and validity, for having high reliability when the potential is tested, which solves the problem in the prior art that the test result does not have reliability and/or validity when a general questionnaire is adopted.

According to one preferred embodiment, the options provided to the subject for feedback by the stimulus information of the ability of handling and operating, the stimulus information of the language competence, the stimulus information of the natural cognition ability, the stimulus information of the artistic ability, the stimulus information of working memory capacity, the stimulus information of information processing ability, the stimulus information of image ability, the stimulus information of music ability, the stimulus information of logic reasoning ability, the stimulus information of spatial ability, the stimulus information of mathematics ability and the stimulus information of thinking transformation ability are set in a way of interval scale and ratio scale. The options provided by the stimulus information to the subject for feedback are set in a way of interval scale and ratio scale. Preferably, whether the feedback information is correct or note is set in a way of interval scale, and the feedback time difference of the subjects is set in a way of ratio scale. The options provided by the stimulus information of the ability to the subject for feedback to organize and manage and the stimulus information of interpersonal skill are set in a way of interval scale. The options provided by this type of stimulus information to the subject for feedback are set in a way of interval scale. Preferably, the options are divided into four classes A, B, C and D, corresponding to scores of 1, 2, 3 and 4, respectively.

According to one preferred embodiment, the stimulus information is sorted according to the type of the stimulus information and/or format of the stimulus information. Preferably, the sorting standard is to the greatest extent an objective standard not susceptible to the subjective factors. For example, the stimulus information is sorted as per information processing class, memory ability class, language class, mathematics ability class. The sorted stimulus information is stored in the stimulus information storing unit 401 of the storing device 400. The stored stimulus information is extracted by the stimulus information providing device 100, and is presented to the subject in a way of visual stimulus information, auditory stimulus information and/or tactile stimulus information. Preferably, the stimulus information in each dimension is provided to the subject in a random sequence. The way of random sequence can simulate the complicated environment stimulus in reality, thereby obtaining the test result more following the real situation.

According to one preferred embodiment, the play speed and/or number of times to play of the stimulus information can be autonomously controlled by the subject through a test system. The visual stimulus information is provided to the subject by the visual stimulus information providing unit 110 of the stimulus information providing device 100. The visual stimulus information providing unit 101 is a computer display, a tablet computer or a mobile phone display screen. The auditory stimulus information is provided to the subject by the auditory stimulus information providing unit 102 of the stimulus information providing device 100. The auditory stimulus information providing unit 102 is an earphone, a sound system or a loudspeaker device. The tactile stimulus information is provided to the subject by the tactile stimulus information providing unit 103 of the stimulus information providing device 100. The tactile stimulus information providing unit 103 is an image tactile device, a sound tactile device or a braille operation device. Preferably, the picture can be the static picture and/or dynamic picture, the time the dynamic picture is completely played once not exceeding 10 seconds. Preferably, the time the video or audio is completely played once not exceeds 1 minute.

According to one preferable embodiment, the stimulus information compiling method of the present invention further includes the following steps: storing the normal physiological feature when the stimulus information is fed back in the physiological feature model unit 404 of the storing device 400.

When the test is performed, the infrared autotracking camera of the control device 300 records the physiological feature presented when the subject feeds back the stimulus information. The recorded physiological feature is compared with the physiological feature index which gives feedback to the corresponding stimulus information and is stored in the physiological feature model unit 404, to determine the reliability level of the feedback given by the subject to the stimulus information. Preferably, the reliability level is determined by matching the physiological feature presented when the subject is tested with the physiological feature stored in the physiological feature model unit 404 and making a feedback to the corresponding stimulus information feedback. The stimulus information feedback with the reliability level higher than 90% is used for calculating the potential evaluation index value.

Figure 3:
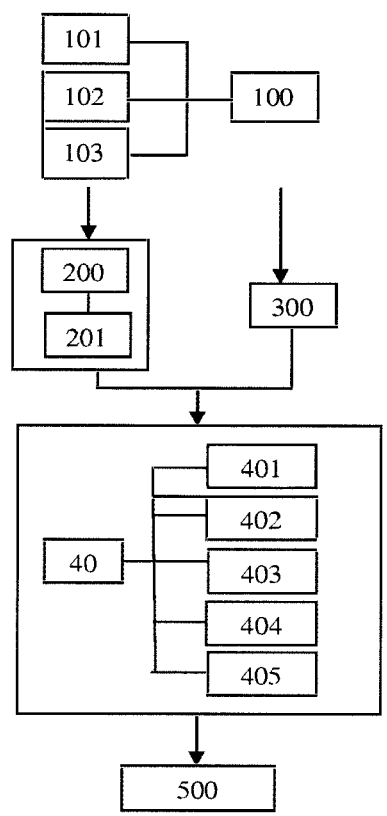
FIG. 3 is a structure schematic diagram of a preferred system to perform tests using the stimulus information of the present invention.

FIG. 3 shows a structure schematic diagram of a system to perform tests using the stimulus information compiling method of the present invention. As shown in FIG. 3, this test system includes a stimulus information providing device 100, a feedback data collecting device 200, a control device 300, a storing device 400 and a data transmitting device 500. The stimulus information providing device 100 provides the stimulus information to the subject. The stimulus information providing device 100 includes a visual stimulus information providing unit 101, an auditory stimulus information providing unit 102 and a tactile stimulus information providing unit 103. The stimulus information providing device 100 can provide the visual stimulus information, the auditory stimulus information and the tactile stimulus information for the subject. The feedback data collecting device 200 collects the feedback of the subject to the stimulus information by its reactor unit 201. The feedback data collecting device 200 sends the feedback to the stimulus information to the storing device 400. The control device 300 records the physiological feature presented when the subject gives the feedback to the stimulus information through the infrared autotracking camera, and meanwhile, the control device 300 records the time the subject gives a feedback to the stimulus information, and sends the recorded information to the storing device 400. The storing device includes the stimulus information storing unit 401, for storing the stimulus information for tests. The response time index storing unit 402 is used for storing the response time index of the feedback on the corresponding stimulus information. The stimulus information feedback unit 403 is used for storing the index value of the feedback on the corresponding stimulus information. The physiological feature model unit 404 is used for storing the normal physiological feature model of the feedback on the corresponding stimulus information. The data analyzing unit 405 is used for make data analysis to each stimulus information index value. After receiving the information sent from the feedback data collecting device 200 and the control device 300, the storing device 400 firstly compares the response time the subject feeds back the stimulus information and the index value stored in the response time index storing unit 402, and further processes the feedback on the stimulus information following the corresponding response time index value. The further processing mentioned herein is to compare the physiological feature presented when the subject gives the feedback to the stimulus information with the model stored in the physiological feature model unit 404, to determine the reliability level of the feedback given by the subject to the stimulus information. The further processing is performed on the feedback on the stimulus information within the range of reliability level. The further processing mentioned herein is to match the stimulus information feedback with the corresponding stimulus information feedback stored in the stimulus information feedback unit 403, to get the index value of each stimulus information feedback of the subject. The obtained index value is summarized by the data analyzing unit 405, to get the potential evaluation index value. The potential corresponding to the potential index value is the potential result of the tested subject. The result is provided to the display device by the data transmitting device 500, for the user to view. According to one preferred embodiment, the display device 500 provides the test result, while the stimulus information is automatically transmitted to the stimulus information providing device 100, the stimulus information providing device 100 provides the next subject to be tested with the stimulus information presented by the subject.

According to one preferable embodiment, the feedback of the subject to the stimulus information is collected to the storing device 400 by the reactor unit 201 of the feedback data collecting device 200. The reactor keys of the reactor unit 201 is made of copper materials with the same gap and sensitivity, such that the feedback data collecting device 200 keeps the constant collecting speed for the stimulus information feedback of the subject. The reactor provided by the present invention has high sensitivity, and overcomes the problem in the prior art that the mouse or keyboard used by the subject has insufficient reaction accuracy and consistency.

According to one preferred embodiment, the present invention selects the brain stimulus information, visual stimulus information, auditory stimulus information and/or tactile stimulus information with high validity according to the normal distribution model. The tactile stimulus information includes the braille tactile stimulus information.

According to one preferred embodiment, the test sequence of the stimulus information is dynamically adjusted based on the physiological information and/or psychological state of the subject, thereby obtaining a real test result of the subject maintaining good psychological states. In order to prevent the subject from feeding back false information due to halfhearted attitude and causing inaccurate test result, the stimulus information compiling method of the present invention further includes collecting the physiological information of the subject in the test and distinguishing his or her physiological states. Lie-detecting the stimulus information further includes presenting forward and backward stimulus information at the same time.

For example, firstly the forward stimulus information is presented that "I will advance bravely in the face of adversity". The feedback information of the subject very accords with his or her situation. Then, the backward stimulus information is presented that "I will never take a risk when I do not feel quite sure about it". If the feedback information of the subject does not accord with his or her situation, the subject is honest; if the feedback information of the subject very accords with his or her situation, the subject is not honest. If the subject is not honest, the stimulus information presented near the lie detection stimulus information is presented repeatedly, and the subject is repeatedly tested. There is a marked word: "please answer after make clear the test".

The presenting speed of the stimulus information is adjusted and controlled according to the response time of the subject in the test recorded by the test system, to be adapted for the test speed of the subject. The present invention can also measure the serious degree of the subject by taking the response time as the index. The way of guiding the subject to adjust the serious degree includes alarming and/or presenting the guiding stimulus information.

The physiological information collected by the present invention includes brain information, facial muscle movement information, eye ball movement information, body action information, acoustic wave information, response time information, pulse information, blood pressure information and/or body temperature information.

The facial muscle movement information includes, but not limited to, the information such as the expression, and the facial muscle activity trace.

The eye ball movement information includes, but not limited to, a visual angle, center visual angle (within 20 degrees), periphery visual angle (outside 20 degrees), fixation coordinate range, fixation time, fixation time discretization, fixation direction, eye ball staying time, eye ball staying range, blink frequency, blink speed, eye closing time, glancing distance, glancing frequency, pupil diameter, fixation mode and number of times of fixation mode.

The body action information includes, but not limited to, deglutition, salivation, saliva constituent, brain wave frequency band, phenomenon related potential, blood pressure, cardiac beat and skin potential.

The acoustic wave information includes, but not limited to, sound volume, tone of sound and speed of utterance.

According to one preferred embodiment, the stimulus information of the present invention includes virtual reality scene information making the subject blend in the real scene, the virtual reality scene information at least including auditory stimulus information, visual stimulus information, olfactory stimulus information and/or tactile stimulus information.

The auditory stimulus information and the visual stimulus information are meanwhile presented to the subject by a virtual reality apparatus, such that the subject feels the interactive real scene, thereby producing the most realistic stress response, to get the accurate test result.

According to one preferred embodiment, the stimulus information is holographic scene stimulus information at least including the auditory stimulus information and the holographic image stimulus information matched therewith, the holographic scene stimulus information presenting the real scene stimulus in a way of three-dimensional stereoscopic image, thereby obtaining the real-time test value of the subject. The holographic image stimulus information includes a static holographic image and a dynamic holographic image.

Second Embodiment

The present invention provides a stimulus information compiling method for personality characteristic value tests following the personality of the eastern. The personality characteristic value evaluation parameter of the subject is acquired by selecting and using the question test and/or scene test following the statistic normal distribution and measured by validity analysis, and the characteristic values of the subject are acquired in at least 27 dimensions from at least five different extents for an ordering index and/or a ratio index of the evaluation parameter.

Figure 11:
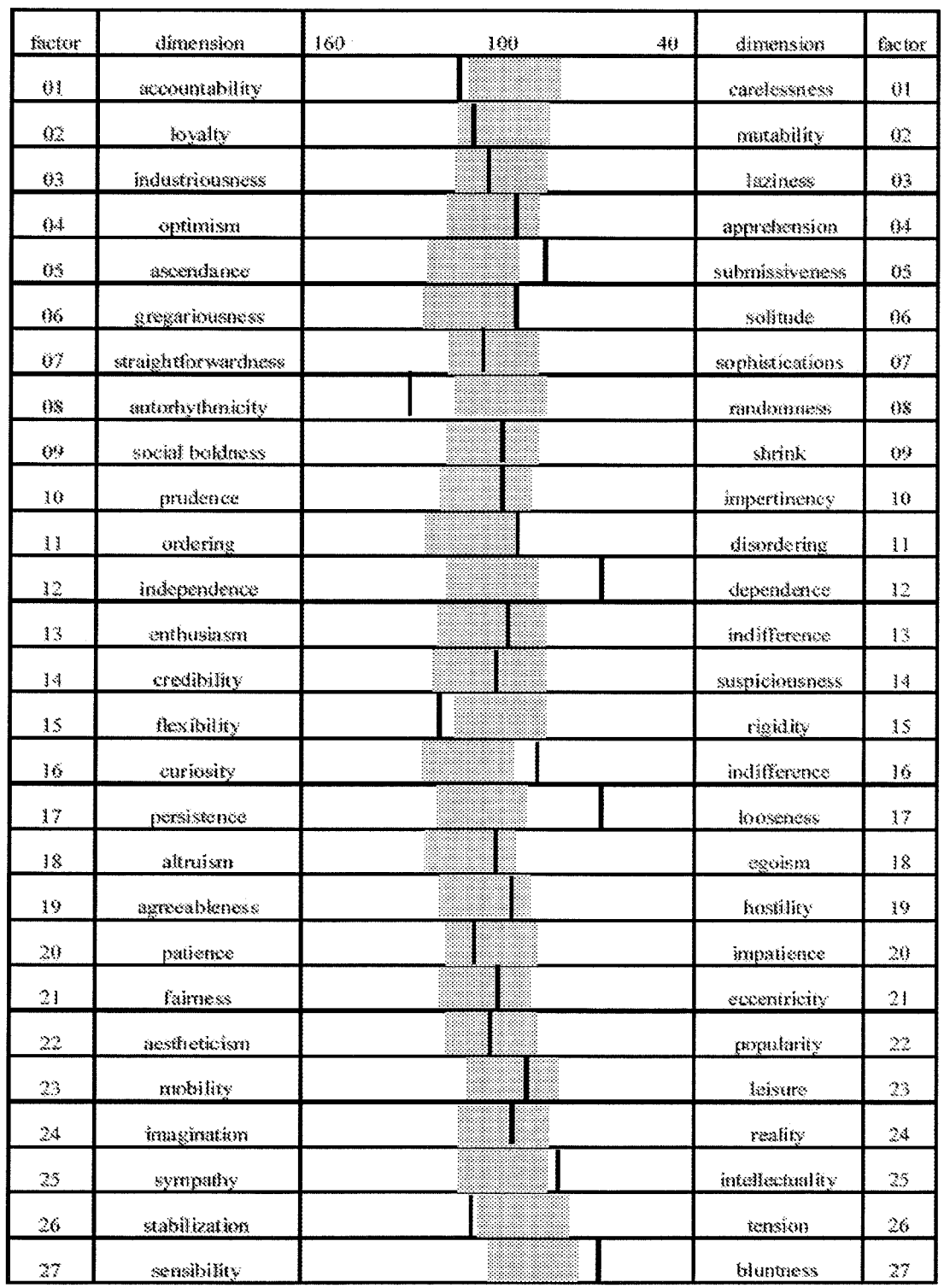
FIG. 11 is a distribution schematic diagram of the cognitive parameter.

According to one preferred embodiment, the question test and/or scene test of each dimension of the at least 27 dimensions at least includes one reverse question;

the validity analysis measure at least includes a discrimination validity measure, an empirical validity measure and a criterion validity measure;

as shown in FIG. 11, the at least 27 dimensions at least includes accountability and carelessness, loyalty and mutability, industriousness and laziness, optimism and apprehension, ascendance and submissiveness, gregariousness and solitude, straightforwardness and sophistications, autorhythmicity and randomness, social boldness and shrink, prudence and impertinency, ordering and disordering, independence and dependence, enthusiasm and indifference, credibility and suspiciousness, flexibility and rigidity, curiosity and indifference, persistence and looseness, altruism and egoism, agreeableness and hostility, patience and impatience, fairness and eccentricity, aestheticism and popularity, mobility and leisure, imagination and reality, sympathy and intellectuality, stabilization and tension, as well as sensibility and bluntness. Each dimension is set with 6 tests, including a backward test. The ordering index is adopted. For example, the dimensions of enthusiasm and indifference is flagged as A, the score of each question in this dimension is respectively flagged as A1, A2, A3, A4, A5 and A6, wherein A4 is the score of the forward question. The total score of enthusiasm and indifference is $A=(A1+A2+A3+A4+A5+A6)/6$. Meanwhile, the response time index and the response time of the subject are recorded, and different response time indexes and the response times reflect different personality character values.

Figure 4:
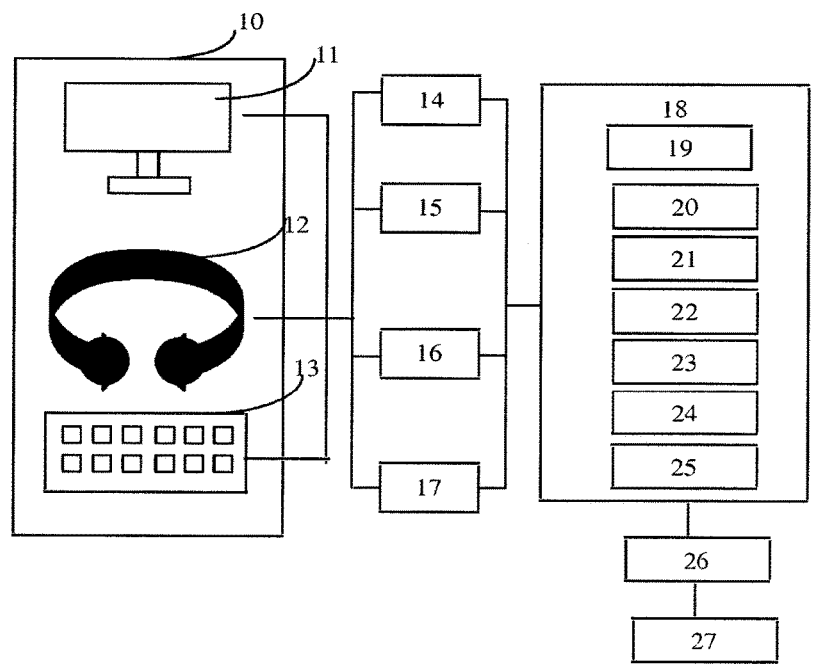
FIG. 4 is a structure schematic diagram of another preferred system to perform tests using the stimulus information of the present invention.

FIG. 4 is a structure schematic diagram of a system to perform tests using the stimulus information compiling method. The present invention further including presenting visual and/or auditory and/or tactile stimulus information to the subject by a stimulus information presenting device 10, recording the body movement change and/or response time index and/or acoustic wave information of the subject in the process of processing the stimulus information by including a response tracking device 17 and a response time control device 14 and/or a sound transmission feedback device 16, the recorded information collectively processed by an analytical processing device 18 and its result fed back to a display device 27. The response tracking device 27 compares the body movement change presented by the subject in the process of processing the stimulus information with each recorded action feature and/or normal action feature by adopting application data and/or an analyzing system through an infrared camera, to record the conversion of the action feature. The present invention further includes recording the response time index of each test item by being connected with the response time control device 14, and detecting in time the serious operation behavior of the subject in a way of alarming. The body movement includes the eye ball movement, facial muscle activity and/or movement of other parts of the body.

The visual presentation stimulus device 11 can be a computer display or a mobile phone screen or a tablet computer screen, the sound presentation stimulus device 12 can be the earphone connected with the computer in a wireless or wired way. The tactile presentation stimulus device 13 can be the braille operation device connected with the computer. The above stimulus information providing device 10 is connected with the analytical processing device 18 by the response time control device 14. The response time control device 14 has the function of adjusting and controlling the test question sequence and the time. When the visual presentation stimulus device 11 is selected, the testee selects the test items to be completed by operating the control device 15, meanwhile, in the test, the response tracking device 17 records the change in action feature of the testee in the test. The above information is respectively stored in the unit corresponding to the analytical processing device 18, the unit of the analytical processing device 18 including a test item unit 19, a response time unit 20, an eye movement track unit 21, a body action unit 22, an acoustic wave message unit 23, an answer unit 24 and a data summarizing unit 25. The above information is transmitted to the display device 27 by the data transferring unit 26 connected in a wireless or wired way after the answer matching and data summarizing are performed on the above information by the analyzing unit. When the sound presentation stimulus device 12 is selected, a sound transmission feedback device 16 responding the sound presentation stimulus is further included. The present invention can be also applicable to standalone tests and network tests.

According to one preferred embodiment, the acoustic wave message unit 23 of the present invention is at least connected with one input device through the sound transmission feedback device 16 (for example, the input device can be an earphone), and is connected with at least one output device such as a microphone. In one preferred embodiment, the acoustic wave message unit 23 can receive the audio input, for example, the voice of the subject, and can output the audio, for example, the instruction displayed on the screen. According to one preferred embodiment, in order to better detect the eye movement track of the subject, at least one infrared LED light and an eye movement tracking camera are mounted on the computer. In the operation, the light emitted from the infrared LED light can directly aim at the front of the cornea of at least one eye of the subject, and is reflected to the eye movement trace recorded by the tracking camera. According to one preferred embodiment, the response tracking device 17 of the present invention further includes recording and capturing the expression and response of the subject for the stimulus information by a video, immediately observing the facial muscle activity and expression of the subject. In order to continuously detect the muscle activity and expression, it is necessary to record the activities of 43 pieces of facial muscle.

The personality characteristic value testing method of the present invention includes the following steps:

generating, by the stimulus information presenting device 10, the test stimulus information in order according to the operation control of the operation control device 15, the subject selecting the degree options of the real situation of the subject according to the test stimulus information;

recording, by the response time control device 14, the response time of the subject during the test; recording, by the response tracking device 17, the actions of the body of the subject during the test; recording, by the sound transmission feedback device 16, the test data of the subject by sound;

performing, by the analyzing device 18, data merge, processing conversion to get the characteristic value of the subject.

Third Embodiment

The embodiment provides a stimulus information compiling method for cognitive ability value tests. The dimensions of the cognitive ability at least include consciousness, memory, attention, concept obtaining, imagination, thought, operation, reasoning, determining, creating, problem addressing, language and meta cognition.

In the psychological test, the validity is the extent to which the measured psychological characteristics accord with, or the accuracy of one psychological test.

Total variance=real variance+error variance=related variance+unrelated stable variance+error variance, that is, $S_x^2 = S_v^2 + S_f^2 + S_z^2$ the validity is defined as the ratio of the real variance (effective variance) related to the measurement to the total variance.

That is, $$r_{xy}^2 = \frac{S_v^2}{S_w^2} = 1 - \frac{S_E^2}{S_w^2} - \frac{S_I^2}{S_w^2}$$

The validity has continuousness, and the test validity is usually denoted by the related coefficient, only different in degree. The value of validity is generally between 0.4~0.7. The greater the value is, the higher the validity is.

Figure 9:
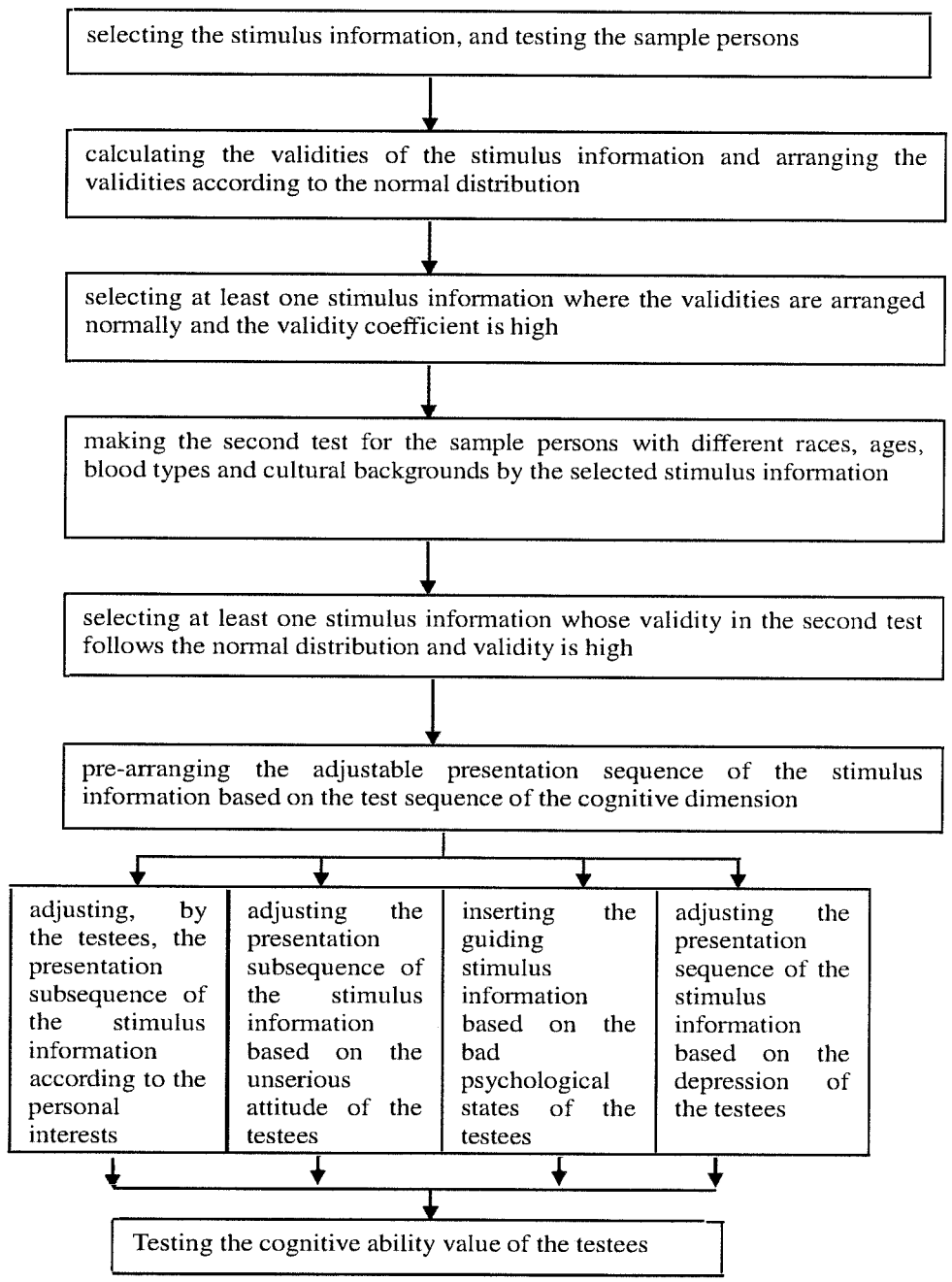
FIG. 9 is a flow chart of the preferred stimulus information compiling method of the present invention.

As shown in FIG. 9, the stimulus information compiling method of the present invention at least includes:

selecting at least one stimulus information of the sample persons whose test validity follows the normal distribution;

setting at least one reasonable sorting based on the validity and cognitive dimension of the at least one stimulus information, for the subject to make a selection according to personal interests;

dynamically compiling lie detection stimulus information and/or aversive stimulus information according to the physiological information and/or psychological states of the subject to test the reliability degree of the subject;

comparing a test score of the subject with that of a valid sample person in a normal distribution model, thereby confirming the distribution of the subject in each cognitive dimension.

Based on each cognitive dimension, the psychological feature parameter is set according to the psychological classical theory. At least one stimulus information is respectively set for each feature parameter. The stimulus information can also be the stimulus information group consisting of a plurality of stimulus information.

The set stimulus information is taken as the preselected stimulus information, and is used for testing the feature parameter corresponding to a large number of sample persons, thereby obtaining the sample validity of the test sample persons.

The present invention tests the sample validity using the normal distribution model.

The sample validity is entered to the standard normal distribution model. The distribution of each cognitive dimension level of the sample persons in the normal distribution diagram is divided into five grades: very bad (5%), relatively bad (20%), general (50%), relatively good (20%), and very good (5%). If the distribution of the sample validity follows the tendency of the normal distribution model, the stimulus information with high validity distributed near the center axis of the model is selected. The stimulus information whose distribution position is closer to the center axis has higher validity.

According to one preferred embodiment, the sample persons are divided into small different groups according to race, age, blood type, and cultural background. Each group of sample persons is tested by the retained at least stimulus information, to obtain the test sample validity of each group of sample persons.

The sample validity is secondarily tested using the normal distribution model. The at least one stimulus information with high validity whose secondary sample validity is distributed in the normal distribution model is retained.

The cognitive dimension values of the sample persons selected by the stimulus information are arranged according to the normal distribution model. The distribution in the normal distribution diagram is divided into five grades: very bad (5%), relatively bad (20%), general (50%), relatively good (20%), and very good (5%).

The stimulus information is sorted according to the cognitive dimension type of the test, and the sequence of presenting the stimulus information is compiled according to the sequence of testing the cognitive dimensions. The test of one cognitive dimension includes the test of a plurality of stimulus information. The score corresponding to the feedback information by the testee is calculated. The distribution areas of the normal distribution model corresponding to the score corresponding to the cognitive dimension are compared, thereby determining the grade corresponding to the cognitive dimension of the testee.

According to one preferred embodiment, the statistic model for selecting the stimulus information of the present invention further includes one or more of a least square model, a perceptron algorithm model, a Boost method model, a hidden Markov model, a Gaussian mixture model, a neural network model and a deep learning model.

The stimulus information is reasonably sorted according to the type of the tested cognitive dimension, and is pre-compiled. There is at least one sorting way. The sorting of the stimulus information is the sorting of different sequences with the same plurality of test effects, thereby being convenient for the subject in normal state to select the sequence of testing cognitive dimensions according to personal interests.

After the stimulus information is sorted, the pre-compiled stimulus information is used for testing the cognitive ability value of the general testees. The test score of the testee is compared with that of a valid sample person in the statistic model, thereby confirming the score distribution of each cognitive dimension of the testee.

Meanwhile, in order to prevent the testee from feeding back false information due to halfhearted attitude and causing inaccurate test result, the stimulus information compiling method of the present invention further includes collecting the physiological information of the testee in the test and distinguishing his or her physiological states. In the test, the present invention can dynamically compile the lie detection stimulus information and/or backward stimulus information according to the physiological information and/or psychological states of the testee, to test the reliability level of the testee.

The lie detection stimulus information can be presented that "I sometimes think about something shameful", and confirm whether the feedback of the testee accords with his or her situation. If the information fed back by the testee is not according with, the testee is not honest.

The presenting speed of the stimulus information is adjusted and controlled according to the response time of the testee in the test recorded by the test system, to be adapted for the test speed of the testee. The present invention can also measure the serious degree of the testee by taking the response time as the index. The way of guiding the testee to adjust the serious degree includes alarming and/or presenting the guiding stimulus information.

If it is found that the testee is not serious, and the information is fed back without reaction to the stimulus information, the test system presenting the stimulus information issues the alarming information, such that the testee will restore the serious attitude.

Or, according to one preferred embodiment, the guiding stimulus information is dynamically inserted based on the physiological information and/or psychological state of the testee, thereby guiding the testee's bad psychological states to restore to be good.

According to one preferred embodiment, a test sequence of the stimulus information is dynamically adjusted based on the physiological information and/or psychological state of the testee, thereby obtaining a real test result of the subject maintaining good psychological states.

If it is found from the collected psychological information parameter that the testee has prolonged response time and slow eye ball movement in the process of testing a certain cognitive dimension, it is determined that the psychological state of the testee is boring. The test system pre-adjusts the subsequent cognitive dimension sequence and adjusts the next cognitive dimension to the cognitive dimension test with relatively relaxing active stimulus information. In this way, the next cognitive dimension tested for the testee will relaxing and interesting, and the psychological states restore to be better.

According to one preferred embodiment, the stimulus information of the present invention further includes virtual reality scene information making the testee blend in the real scene, the virtual reality scene information at least including auditory stimulus information, visual stimulus information, olfactory stimulus information and/or tactile stimulus information.

The auditory stimulus information and the visual stimulus information are meanwhile presented to the testee by a virtual reality apparatus, such that the testee feels the interactive real scene, thereby producing the most realistic stress response, to get the accurate test result.

According to one preferred embodiment, the stimulus information is holographic scene stimulus information at least including the auditory stimulus information and the holographic image stimulus information matched therewith, the holographic scene stimulus information presenting the real scene stimulus in a way of three-dimensional stereoscopic image, thereby obtaining the real-time cognitive ability test value of the testee; the holographic image stimulus information including the static holographic image and the dynamic holographic image.

The auditory stimulus information and the three-dimensional stereoscopic holographic image are meanwhile presented to the testee. The senses of the testee are activated, and the vivid scene mode is beneficial for the testee to quickly show the real level of the cognitive ability. The testee can also speak to express his or her feedback behavior or psychological feelings.

When the olfaction stimulus information and the three-dimensional stereoscopic dynamic holographic image are meanwhile presented to the testee, for example, a stranger invites the testee to taste delicious food, the testee will give the real test answers based on his or her behavior, instead of recalling the daily life, and then giving the test answer after thinking carefully. Therefore, the auditory stimulus information, the olfaction stimulus information and the visual stimulus information are compiled together, which is more beneficial to obtaining the accurate result of the cognitive ability value test.

Fourth Embodiment

Figure 10:
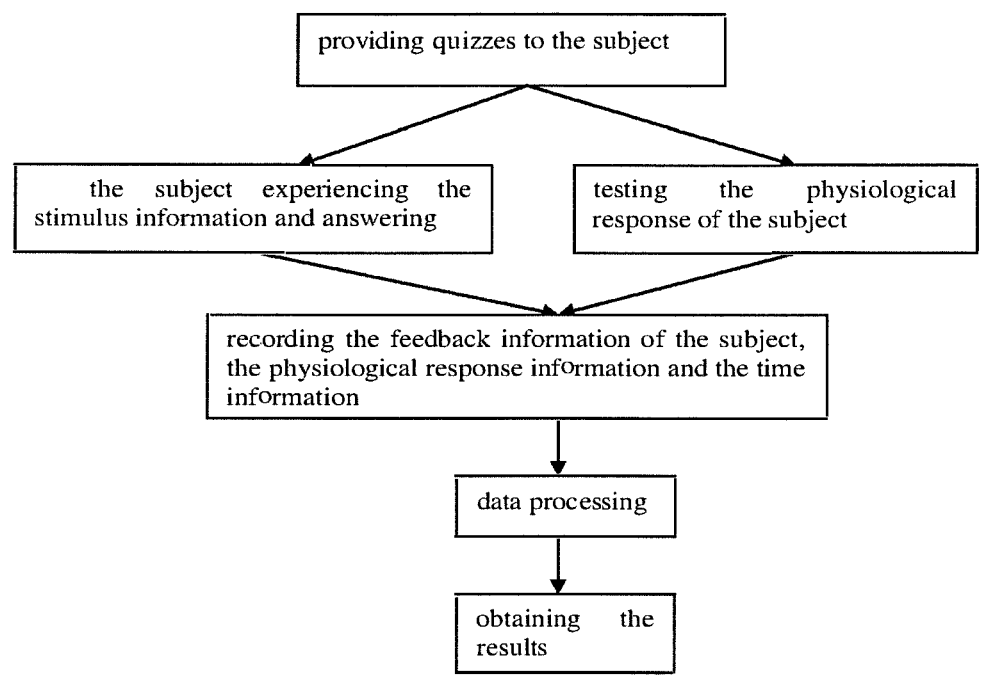
FIG. 10 is a flow chart of the preferred interest orientation value testing method of the present invention.

The embodiment provides an interest orientation value testing method. As shown in FIG. 10, the interest orientation value testing method includes the following steps:

(1) providing quizzes to the subject, the quizzes containing the stimulus information related to the potential interest of the subject, and a plurality of descriptions of the stimulus information.

The stimulus information contains the static picture, dynamic picture, video and audio, described as the objective description on the contents in the picture. The picture contains a plurality of things. The description objectively explains one or more things contained in the picture. The subject selects the descriptions following the observed or concerned thing according to his or her understanding.

According to one preferred embodiment of the present invention, the description further contains the five-point inventory tendentious description, for example, under the scene provided by the stimulus information, five tendentious descriptions of the subjective feeling or evaluation of the subject similar as: "strongly agree", "agree", "uncertain", "disagree", "strongly disagree", or "like very much", "like", "indifferent", "do not hate", "hate very much", or the actions probably taken by the subject in the practical actions. The subjective feelings of the subject to the stimulus information can be obtained by the five-point inventory questionnaire, and the subjective feelings are matched with the detected physiological response information when the subject experiences the stimulus information, for providing a certain reference for the emotional determination of the subject. The five tendentious descriptions are respectively assigned with five scores 5, 4, 3, 2, 1. The tendentiousness total score of the subject to each type of stimulus information is the sum of the scores of the feedback information of the subject to each stimulus information in this class. The tendentiousness score of the subject to each stimulus information is recorded as L.

(2) selecting, by the subject, one or more descriptions for each quiz according to his or her own understanding, as the feedback information of the subject; meanwhile, the physiological response information and time information of the subject to the stimulus information.

The play speed and/or number of times to play of the stimulus information is autonomously controlled by the subject, thereby reflecting the attention time of the subject to the stimulus information.

The physiological response information is one or more of pupil diameter, galvanic skin response, pulse, blood pressure, and brain wave information of the subject.

According to one preferred embodiment of the present invention, the physiological response information includes the pupil diameter information and the galvanic skin response information of the subject. Two physiological response information are combined, and are verified and supplemented mutually, such that the test result is more accurate.

(3) recording and storing the feedback information of the subject, the physiological response information and time information, for the subsequent data processing.

According to one preferred embodiment of the present invention, the time information includes the experience time of the subject to certain stimulus information and/or the duration time of a certain physiological response. The experience time is the time from the subject starts experiencing the stimulus to the subject ends experiencing the stimulus and enters the next quiz, which possibly reflects the attention time of the subject to the stimulus information to some extent. The experience time can be simplified as the time the subject answers each quiz.

The duration time of the physiological response is time from the subject has some emotion, and causes the psychological information related thereto to start to change to the psychological information restores to be normal or suddenly changes to another stronger emotion. In order to judge whether the change is the end or strengthening of the previous emotion, it is necessary to refer to the feedback information of the subject when the two emotions occur.

According to one preferred embodiment of the present invention, the stimulus information is sorted according to the content contained in the stimulus information in advance. The sorting standard of the contents is to the greatest extent an objective standard not susceptible to the subjective factors. For example, the stimulus information is sorted as per music class, sports class, mathematics class and literature class, and so on. Provision to the subject is realized according to the order that several types of stimulus information are random, and/or in a way of the same type of stimulus information continuously provided to the subject. The way of random sequence can simulate the complicated environment stimulus in reality, thereby obtaining the data more following the real situation. The way of the same type being continuous can more clearly observe the influence extent of the emotion response to the subject by the stimulus information, and the interest keeping situation according to the duration time of a certain emotion response of the subject. The stimulus information is matched with the physiological response time and the time information, to get the experience time, the physiological response and duration time of the subject to each type of stimulus information. By comparing the responses of the subject under different types of stimulus, the subject interest orientation is initially obtained.

(4) processing the stimulus information, the feedback information of the subject, the physiological response information and time information, to eventually get the interest orientation result of the subject.

According to one preferred embodiment, the objective description of each quiz belongs to the main class of the stimulus information. For example, the stimulus information is pre-divided into the sports class, a plurality of sports apparatuses are contained in the stimulus information, the optional objective descriptions occurring in the quiz are respectively the names of these sports apparatuses, such as table tennis bats, a football, a basketball and a shuttlecock. Therefore, the feedback information of the subject reflects the tendentious cognition of the subject to the stimulus information. The stimulus information is grouped according to the stimulus information of the subject. Therefore, grouping according to the feedback information can know the number of the stimulus information judged to be the same type by the subject himself or herself, and the thing information which is more easily focused by the subject under different backgrounds by analyzing the stimulus information. The grouped stimulus information is matched with the physiological response information and the time information, to get the experience time, the physiological response and the duration time of the subject to each type of stimulus information.

The experience time, the physiological response and the duration time of each type of stimulus information and each group of stimulus information are respectively quantized, and are given with different weights.

The physiological response is a difference value between the physiological data and a base line. The base line is the physiological state under the ordinary states when any stimulus is not made to the subject. Before test, it is necessary to measure the physiological data of the subject under the ordinary state, to determine the base line.

Since the galvanic skin response and the pupil diameter test are performed at the same time, for each group of stimulus information, there are correspondingly two function curves regarding the time t, that is, the skin conductivity curve A (t), and the pupil diameter changing curve B (t). The time the subject experiences each stimulus information is recorded as T. The definite integral is performed on the skin conductivity curve A (t) and the pupil diameter changing curve B (t) when the subject experiences each stimulus information with respect to the time, to get the skin conductivity information A and the pupil diameter information B of the subject to each stimulus information.

The physiological response duration time of the subject to each stimulus may be different, some may continue to the next stimulus information or even longer, and some may end before entering the next stimulus. For ease of calculation, for the physiological response ending before the stimulus ends, the duration time is recorded as from the physiological information starts changing to it restores to be normal. For the physiological information restoring to be normal until the next stimulus, the physiological response duration time of the first stimulus information is recorded as from the physiological information starts changing to the stimulus ends, and the physiological response duration time of the second stimulus information is recorded as from the stimulus starts to the physiological response ends. For the physiological information continues and suddenly changes to another stronger physiological response, the duration time is recorded as from the physiological information starts changing to it suddenly changes.

The physiological response duration time of the subject to each stimulus is t. The number of the stimulus information in each main class is recorded as N. In the group divided according to the feedback information of the subject, the number of the stimulus information in each group is recorded as n. The interest tendentiousness value of the subject to each stimulus information is a function of five element parameter, that is φ=(xL,yA,zB,pT,qt), wherein x, y, z, p, q are weighting parameters. The average interest tendentiousness value of the subject to the stimulus information in each group is $P_n=(\varphi_1+\varphi_2+\varphi_3+ \ldots +\varphi_n)/n$. The average interest tendentiousness value of the subject to the stimulus information in each main class is $P_N=(\varphi_1+\varphi_2+\varphi_3+ \ldots +\varphi_N)/N$. Practically, it tends to differently determine the normal state of the subject, such that the base line is not accurately selected, and harmful effects are caused on the interest orientation value tests to the subject. It is possible to obtain the relatively accurate data by averaging all data in the whole test process. The number of all stimulus information is recorded as K, and then the average interest orientation value of the subject to each stimulus information is $P_K=(\varphi_1+\varphi_2+\varphi_3+ \ldots +\varphi_K)/K$. The information of the group divided according to the feedback information of the subject is also an important index to judge the interest orientation, and it is necessary to take it as a parameter to be considered. The orientation value of the subject to each group of stimulus information is $W=(P_n, P_N, P_K, n, N, K)$.

According to one preferred embodiment of the present invention, the time the dynamic picture in each stimulus information is completely played once does not exceed 10 seconds, and the time the video or audio in each stimulus information is completely played once does not exceed 1 minute. In data processing, the stimulus information is classified into several main classes in the way of pre-classification according to the objective standards, and then divided into small classes according to the format of stimulus information, for example, the formats of the static picture, the dynamic picture, the video, and the audio are respectively classified into different types. For ease of calculation, it is usual to provide each main class and each small class of stimulus information according to the same number. One part of the stimulus information is provided to the subject in a random order, and the other part is provided to the subject in an order of continuously playing the same class of stimulus information.

The time the subject observes each static picture, and the number of times of playing each dynamic picture, video or audio shall be recorded as time information. For the behavior that the subject changes the normal play when the stimulus information is played, the operations such as playback, fast forward and pause shall be recorded as the special time information.

In addition, the facial expression identification information can be taken as the physiological information of the subject. Without the interference by other environments, for example, the subject controls his or her emotion on his or her own in some cases, and the natural and unconscious facial expression of the subject may be simultaneous with his or her emotion, which can relatively intuitively reflect his or her inner emotion. As for the interest test, it is not necessary to more deeply analyze the expression, and it only needs to determine the subject's base emotions such as enjoyment, aversion, and whether to be concentrated on feeling the stimulus information, which is sufficient to meet the requirement of interest test. If the emotion information of the subject is acquired by a Noodas facial expression identification analyzing system, this emotion information is quantized to obtain the emotion data of the subject, and is taken as the physiological data to be applied to the calculation of the interest tendentiousness value.

The experience time, the physiological response and the duration time of the subject to the stimulus information are classified according to the objective standard of the stimulus information and the format of the stimulus information, and are divided into small groups according to the feedback information of the subject. The experience time, the physiological response and the duration time of the subject are matched with the stimulus information, by comparing the experience time, the physiological response and the duration time corresponding to each group of the stimulus information in the same class, the interest tendentiousness of the subject is determined. Or, the experience time, the physiological response and the duration time are quantized, to get the interest tendentiousness of the subject.

In addition, the stimulus information similar to the subject physiological response is screened, and/or the stimulus information similar to the subject experience time is screened, and/or the stimulus information similar to the duration time of the subject physiological response is screened. The stimulus information is classified according to the physiological response type of the subject, and/or the experience time of the subject, and/or the duration time of the subject physiological response, and the similarity and/or difference of the stimulus information in the same class are compared. The comparison result is used as a reference or a judging standard of the subject interest tendentiousness test. The stimulus information containing the same interest matter of the subject causes the same or similar physiological response of the subjects. Therefore, the stimulus information to which the subjects respond the same usually contains the same type of matter, which can relatively obviously influence the physiological response of the subject. The matter interested by the subject can be obtained by analyzing the same type of matter, for measuring the interest orientation value of the subject in an auxiliary manner.

Fifth Embodiment

This embodiment is an improved embodiment to any of the embodiments. This embodiment provides a method for encrypting and transmitting the stimulus information test value based on the stimulus information compiling method. The stimulus information test value is sent to the analytical processing device/server. The remote analytical processing device/server generates a test report, is encrypted and is sent to the client.

According to one preferred embodiment, the remote analytical processing device/server generates a test report, is encrypted, and is sent to the client. When the remote analytical processing device/server encrypts the generated test report, a first key managing module pre-storing at least one key pair randomly generates a first flag value representing the encryption key. A first encryption module pre-storing at least one encryption algorithm converts the test report to a first cryptograph according to its randomly selected encryption algorithm and the first flag value, the encryption module having therein a second flag value corresponding to the encryption algorithm one by one. The first transmission module sends the first cryptograph, the first flag value and the second flag value to a client. The client converts the first cryptograph to the plaintext test report according to the first flag value and the second flag value.

The "cryptograph" in this embodiment refers to the information which is obtained after the encryption algorithm and the key processing and cannot be directly understood. The "plaintext" refers to the information which can be directly understood. The "first flag value" refers to the parameter for flagging the key, such as 1, 2, 3 or A, B, C.

The "second flag value" in this embodiment refers to a parameter for representing the encryption algorithm, and can be a combination of numerals and letters, such as a, b, c or A1, B2, C3.

The "key pair" in the embodiment refers to the encryption key and the decryption key mutually matched.

The "decryption module" in this embodiment includes a first decryption module and a second decryption module.

The "encryption module" in this embodiment includes a first encryption module and a second encryption module.

The "key managing module" in this embodiment includes a first key managing module and a second key managing module.

The "transmission module" in this embodiment includes a first transmission module and a second transmission module.

Figure 5:
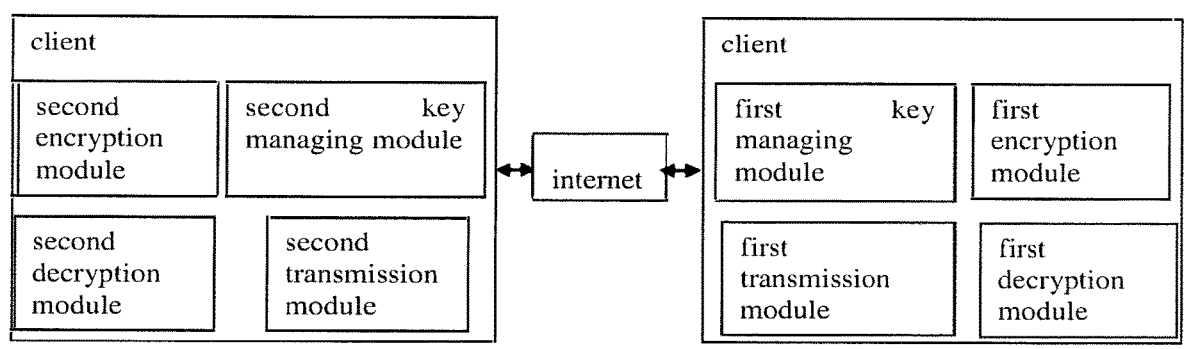
FIG. 5 is a structure schematic diagram of the device for performing the encryption method of the present invention.

FIG. 5 shows a structure schematic diagram of the device for performing the method of the present invention. The device includes a client for providing the quizzes to the testee, and a remote server for analyzing the data to generate the test report, the client and the remote server transferring the information over the internet.

The client is provided with a second encryption module for encrypting the test answers; the second key managing module for randomly generating the first flag value; the second decryption module for decrypting the encrypted test report; and the second transmission module for transmitting the encrypted test answer and receiving the encrypted test report. The remote server is provided with a first encryption module for encrypting the test report, a first key managing module for randomly generating the first flag value, a first decryption module for decrypting the encrypted test answer, and a second transmission module for transmitting the encrypted test report and receiving the encrypted test answer.

The first encryption module and the second encryption module pre-stores therein at least one same encryption algorithm, including a symmetrical encryption algorithm and an asymmetrical encryption algorithm. The symmetrical encryption algorithm means that the keys used by the encryption and decryption are the same, for example, the data encryption algorithm (DES), the international data encryption algorithm (IDEA), RC2 algorithm and RC4 algorithm. The asymmetrical encryption algorithm means that the keys used by the encryption and the decryption are different, the key used by the encryption referred to as a public key, and the key used by the decryption referred to as a private key, for example, the RSA algorithm, the Elgamal algorithm, the knapsack algorithm, Rabin, the D-H algorithm, the advanced encryption algorithm AES and the elliptic curve encryption algorithm ECC.

Figures 6, 7, 8A:
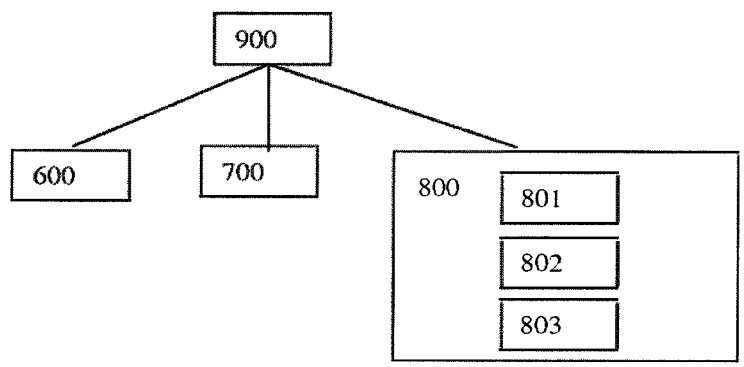
FIG. 6 is a data storage mapping diagram of the encryption module of the present invention.
FIG. 7 is a data storage schematic diagram of the encryption managing module of the present invention.
FIG. 8A is a schematic diagram of the driver top speed assessing system of the present invention.

As shown in FIG. 6, the encryption module sets a second flag value corresponding thereto one by one for each encryption algorithm.

The decryption algorithm matched with the encryption algorithm in the encryption module is pre-stored in the decryption module, and the identical second flag value is set for the matched encryption algorithm and the decryption algorithm. Specifically, the decryption algorithm is the inverse operation of the encryption algorithm.

As shown in FIG. 7, the decryption key matched with the encryption key is stored in the key managing module, for example, the keys adopted by the encryption and decryption in the asymmetrical encryption are different. Moreover, a plurality of mutually different keys is stored in the encryption module, thereby increasing the difficulty of the decodable information. The first encryption module and the second encryption module store the same key pair and the first flag value. The key managing module is protected by firewall, thereby making the stored key not be read illegally, particularly, the private key in the asymmetrical key.

The key managing module is connected with the encryption module. When the encryption module encrypts the data, the key managing module randomly generates one first flag value representing the encryption key, and the encryption module encrypts the data based on the randomly selected encryption algorithm and the randomly generated encryption key, and sends out the first flag value corresponding to the encryption key and the second flag value corresponding to the encryption algorithm together with the encrypted cryptograph, which avoids the key being transmitted publicly over the network, and increases the data security.

The device further includes an authentication module which is provided at the client, the personal information of the user such as the fingerprint information, the retina information, and the wave information of the user pre-stored in the authentication module. The testee can extract the test report after entering these personal information through the authentication module at the client. Further, the authentication module can further identify and confirm the true-false of the test report, in order to examine and check the legality and authenticity of the information, so that except for the legal sender of the test report, for example, the server side in the present invention, other third parties cannot counterfeit the legal test report, which ensures that the information of the test report is not maliciously tampered by the third parties, and the legal test report cannot be replaced with the counterfeit test report.

According to one preferred embodiment, for the testee tested remotely, the test report or the test answer needs to be sent to the client or the server side through a plurality of nodes. Therefore, in order to further ensure the test report or the test answer is not intercepted or tampered by the third party during transmission, which not only encrypts the main body, but also encrypts the routing information, the control information and the checkout information. When the first cryptograph or the second cryptograph is sent out by the transmission module, the encrypted routing information, control information and the checkout information are additionally sent. After one node receives the first cryptograph or the second cryptograph, it needs to perform decryption to obtain the routing information and the checkout information, to perform the route selection and the error detection. Then, the key of the next link is used to encrypt the first cryptograph or the second cryptograph, to be transmitted.

Sixth Embodiment

Figure 8B:
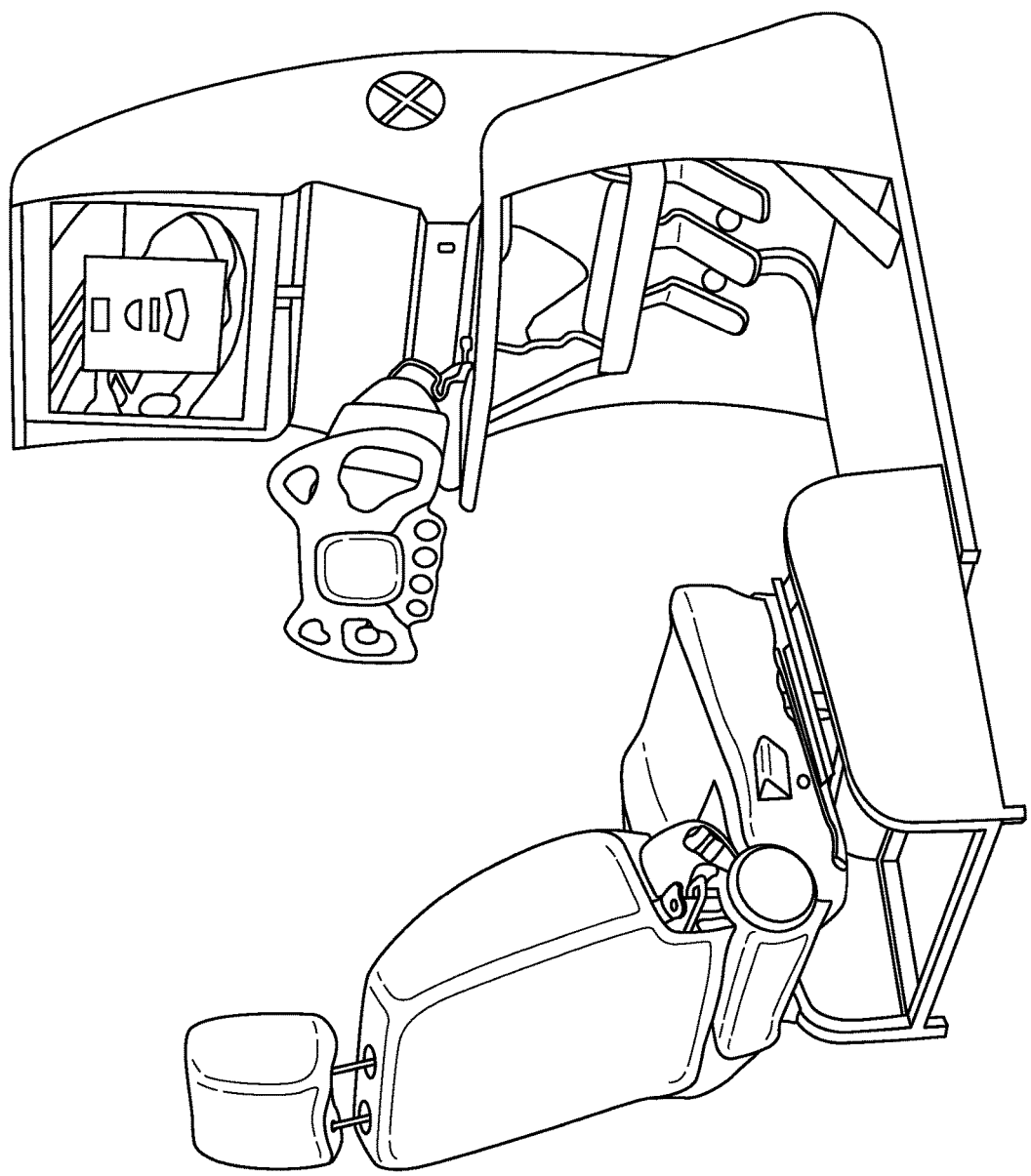
FIG. 8B is a picture the driver top speed assessing system of the present invention.

As shown in FIG. 8, the embodiment is a driver top speed assessing system formed by using the stimulus information compiling method. The driver top speed measuring system includes: a stimulus information generating module 600, a feedback information collecting module 700, a speed analyzing module 800 and a center control device 900.

The stimulus information generating module 600 is used for generating the stimulus information consisting of sound, image, video and/or vibration displacement to the subject. Specifically, the stimulus information generating module 600 at least includes the display device and the speaker device. Preferably, the display device can be a client mobile terminal. The display device can also be a mobile phone with the present system APP. The display device can further be a vehicle display device. When it is necessary to generate the stimulus information of the vibration displacement, the stimulus information generating module 600 further includes a driving device.

The feedback information collecting module is used for collecting the feedback information initially given by the subject and/or given in response to the stimulus information. The feedback information collecting module 700 includes a steering wheel with buttons, a pedal plate, a mobile phone receiver, a network transmission device, a camera and an eye tracker.

The speed analyzing module 800 includes a response speed unit 801, an attention extent unit 802 and a hand-foot-eye coordinating unit 803. The speed analyzing module 800 can make an analysis based on the stimulus information and the feedback information and in combination with the stored standard database to obtain the top speed of the subject.

The center control device 900 is a device with the calculating unit and the storing unit, for example, the center control device 900 of the present invention can be a local computer host or a distributed cloud server. Preferably, the standard database of the present invention is stored on the storing unit of the center control device 900. The standard database at least includes: the standard speed data, the attention threshold data and the coordination data.

The center control device 900 is respectively connected with the stimulus information generating module 600, the feedback information collecting module 700 and the speed analyzing module 800. The center control device 900 can control the generation of the stimulus information, the collection of the feedback information and the analysis output of the top speed according to the test needs. For example, the display device and the speaker device in the stimulus information generating module 600 output the stimulus information consisting of sound, image and/or video according to the control signal outputted by the center control device 900. The feedback information collecting module 700 regularly or irregularly collects the feedback information according to the time index of the stimulus information outputted by the stimulus information generating module 600 and/or a sampling instruction sent by the center control device 900, and transmits them to the speed analyzing module 800 under the control of the center control device 900.

The driver top speed assessing system of the present invention has the following operation principle.

After the test starts, the stimulus information generating module 600 produces the stimulus information to the subject through its display device, speaker device and/or driving device under the control of the center control device 900. The stimulus information includes sounds, image and video. Preferably, the stimulus information further includes the vibration displacement.

The feedback information collecting module 700 collects the feedback information of the subject. The feedback information is initially given by the subject, or is given by the subject in response to the stimulus information. The feedback information collecting module 700 collects the feedback information through the steering wheel, the panel plate, the mobile phone receiver, the network transmitting device, the camera and the eye tracker, the feedback information including the operation action, the eye movement index and the head movement index of the subject. The feedback information collecting module 700 stores the collected feedback information or send to the speed analyzing module 800.

The response speed unit 801, the attention extent unit 802 and the hand-foot-eye coordinating unit 803 respectively calculates the first, second and third data according to the stimulus information and the feedback information and in combination with the standard database. The speed analyzing module obtains the top speed after performing the weighting process on the first to third data.

Specifically, the first data is related to the response speed and the emergency response speed of the subject. When the first data is measured, the stimulus information generating module 600 generates sound, image and/or video information for measuring the response speed. The feedback information collecting module 700 samples the first feedback information fed back by the subject in response to the stimulus information, and respectively records its time data. The first feedback information at least includes the operation action and the eye movement index. The response speed unit 301 processes the first feedback information with the time data, to get the response speed and the emergency response speed of the subject, and gets the first data after weighting.

The second data is related to the attention extent of the subject. When the second data is measured, the display module of the stimulus information generating module 600 respectively generates the first and second visual stimulus information at the central field of view and the peripheral field of view of the subject. The first and second visual stimulus information performs the cross transform in a way of descending time period, thereby making the subject correspondingly give feedback to the visual stimulus information with different difficulty levels. The feedback information collecting module 700 samples the operation action, head movement index and eye movement index of the subject, and takes them as the second feedback information to be stored. The attention extent unit 302 makes an analysis according to the second feedback information, the first and the second visual stimulus information and in combination with the attention threshold data in the standard database to obtain the second data. Preferably, the stimulus information further includes the sound stimulus. The brain wave measuring device of the feedback information collecting module 700 measures the brain wave signal of the subject, the second feedback information further containing the brain wave data, which can further increase the accuracy of the attention extent the depth measurement.

The third data is related to the hand-foot-eye coordinating ability of the subject. When the third data is measured, the display device of the stimulus information generating module 600 generates a simulative driving scene periodically changing with time, so that the subject performs the simulative driving operation. The simulative driving scene at least includes three operation difficulty levels. The feedback information collecting module 700 collects the hand action, foot action, and eye movement index of the subject, and stores them as the third feedback information. The hand-foot-eye coordinating unit 303 makes an analysis according to the third feedback information and/or the driving simulated data and in combination with the coordination data in the standard database to obtain the third data.

According to one preferred embodiment, the response speed measuring method is that: the display device of the stimulus information generating module 600 provides the subject with at least one stimulus information, and the subject gives the corresponding feedback to the stimulus information. Meanwhile, the feedback information collecting module 700 samples the feedback information of the subject, and records the feedback time of the subject.

According to one preferred embodiment, the emergency response speed testing method is that: one moving object analogue appears on the display device of the stimulus information generating module 600 and moves forward on the display device, one object suddenly appears at the front left or right of the moving object, and the subject needs to make a response of avoiding or stopping moving. The feedback information collecting module 700 samples the feedback information of the subject, and records the feedback time of the subject.

According to one preferred embodiment, the attention extent testing method is that: a three-digit number appears on the display device of the stimulus information generating module 600, this number stays on the display device for 1 second, and after the number disappears, it needs for the subject to say the disappeared three-digit number. If the answer of the subject is correct, a four-digit number continuously appears on the display device, this number stays on the display device for 1 second, and after the number disappears, it needs for the subject to say the disappeared four-digit number. If the answer of the subject is correct, the digit of the number is continuously increased, until the subject makes a mistake for three times in the memory of that number. The feedback information collecting module 700 samples how many digits the subject can remember eventually.

According to one preferred embodiment, the hand-foot-eye coordination testing method is that: the display device of the stimulus information generating module 600 provides the subject with at least one stimulus information, and the subject gives the corresponding action feedback according to the stimulus information instruction. Meanwhile, the feedback information collecting module 700 samples the feedback information of the subject, and records the feedback time of the subject.

According to one preferred embodiment, the emotion control testing method is that: the picture stimulus information capable of producing different emotions appears on the display device of the stimulus information generating module 600m, for example, snakes, mice and miserable situation of car accidents or disaster scenarios. The subject makes the corresponding control feedback according to the stimulus information instruction. Meanwhile, the feedback information collecting module 700 samples the feedback information of the subject, and records the feedback time of the subject.

According to one preferred embodiment, the personality stability testing method is that: the stimulus information generating module 600 provides one dangerous scene stimulus information and tells the subject that it needs to finish the corresponding actions within several seconds. For example, several keys are given, and the subject is required to open one door within 30 seconds. Meanwhile, the feedback information collecting module 700 samples the feedback information of the subject, and records the feedback time and the eye movement index of the subject.

According to one preferred embodiment, the driver top speed assessing system and method provided by the present invention obtains the top speed in the following way.

The feedback time of the subject is divided into the following four stages: (1) the stage from the subject receiving the stimulus information to the subject sending the instruction (T1); (2) the stage of the subject moving his or her feet to the brake pedal (T2); (3) the stage of the idle stroke of the pedal (T3); (4) the stage of the braking force increasing (T4). The response time of the subject plus the automobile braking time (T5) is generally 0.3~0.8 second. The calculation method of the total time is $T=\Sigma_n T n$. The total sliding distance=T*V.

For example, the vehicle speed is 120 kilometer per hour, T is 3.3 seconds, and then the total sliding distance=(120*1000)/60/60*3.3=110 m.

That is, a certain driver sees a certain object 100 meters away, makes a response to brake the automobile immediately, and the automobile will rush out by 110 meters, which means that he needs to make a response to brake the automobile 110 meters away.

The above each item of cognitive index value standard score and the response accuracy standard score are added, to obtain one composite Z score; the composite Z score is converted to the T score representing the response ability level state of the subject. This T score is the quantized value of the response ability. Then, according to the total T score of the response of each driver, by being compared with a norm, three standard speeds of each driver are given: the blue speed (safe speed), yellow speed (alarming speed), and red speed (dangerous speed).

According to one preferred embodiment, the speed analyzing module 800 further includes an emotion analyzing unit. The stimulus information generating module 600 gives the stimulus information which contains video and vibration displacement and changes according to the time period, for example, the scenes easily causing the emotional fluctuation of the driver such as the simulated traffic jam, slight impact, the driver of the leading vehicle driving on the wrong side of the road.

The feedback information collecting module 700 collects the micro expression data and/or brain wave data of the subject, and takes them as the fourth feedback information. The emotion analyzing unit makes an analysis according to the stimulus information, the fourth feedback information and the emotion data in the standard database and gets the emotion control data of the subject. The speed analyzing module 800 performs the weighting processing on the first to third data and the emotion control data and then gets the top speed. By the test of the emotion control ability of subject, the simulative scene is closer to the practical driving scene, which can increase the practicability and accuracy of the top speed test.

According to one preferred embodiment, the speed analyzing module 800 further includes a driving behavior judging unit. The driving behavior judging unit makes an analysis according to the feedback information and the stimulus information to obtain the driving behavior data of the subject. The driving behavior data at least includes the following distance and the relative speed, and the speed analyzing module 800 can correct the top speed according to the driving behavior data. During the practical driving, the driver usually has different driving habits, whereas these driving habits have significant effects on the driving security. The driving behavior judging unit makes an analysis to obtain the driving behavior data of the subject, such that the speed analyzing module 800 corrects the top speed according to the driving behavior data.

According to one preferred embodiment, the standard database further includes an empirical distribution model whose related indexes are the age and top speed. The empirical distribution model is obtained by a great number of tests, for example, the detection is performed by the driver top speed assessing system of the present invention. The speed analyzing module 800 makes an analysis according to the age of the subject and the measured top speed and in combination with the empirical distribution model in the standard database to get the predicted top speed of the subject within one measurement period.

The technical solution of the present invention is not limited to the technical solution disclosed in the above embodiments, and the technical means of the above embodiments can be combined one another to form new technical solutions.

It should be noted that the above specific embodiments are exemplary, persons skilled in the art can devise various solutions under the inspiration of the disclosed content of the present invention, and the solutions also belong to the disclosed scope of the present invention and fall into the protection scope of the present invention. Persons skilled in the art shall understand that the specification and its drawings of the present invention are exemplary and do not limit the claims. The protection scope of the present invention is limited by the claims and its equivalents.

What is claimed is:

1. A driver speed assessing system
   a stimulus information generating module comprising a display device, a speaker and a driver seat with vibration function, wherein the stimulus information generating module generates sound, image and vibration stimulus to a test subject; wherein the stimulus information generating module is configured to generate a first set of stimulus to test the subject's response speed, a second set of stimulus to test the subject's attention span, and a third set of stimulus to test the subject's hand-foot-eye coordination,
   a feedback information collecting module comprising a steering wheel with buttons, a foot pedal, a mobile phone receiver, a network transmission device, a camera, an eye movement tracker, and a brain wave measuring device, wherein the feedback information collecting module records the test subject's response information to the sound, image and vibration stimulus provided by the stimulus information generating module, wherein the recorded response information comprises the test subject's eye movement and head movement, wherein the feedback information collecting module collects a first set of response data corresponding to the subject's response to the first set of stimulus, a second set of response data corresponding to the subject's response to the second set of stimulus, and a third set of response data corresponding to the subject's response to the third set of stimulus;
   a speed analyzing module comprising a response speed unit that process the first set of response data to determine the subject's response speed and emergency response speed, an attention extent unit that process the second set of response data to determine the subject's attention extent and the depth, and a hand-foot-eye coordinating unit that process the third set of response data to determine the subject's hand-foot-eye coordination ability, wherein the speed analyzing module determines a top speed of the subject based on the first, second and third set of data and provides three speed limits to the test subject: a safe speed limit, an alarming speed limit and a dangerous speed limit;
   a central control module that controls the a stimulus information generating module, the a feedback information collecting module and the a speed analyzing module, analyze collected data and determines output.

2. The driver top speed assessing system of claim 1, wherein the stimulus information generation module is configured to generate visual and vibration stimulation that causes emotional fluctuation of a driver.

3. The driver top speed assessing system of claim 1, wherein the feedback information collecting module is configured to collect facial expression data and brain wave data from the test subject.

* * * * *